US007983743B2

(12) United States Patent
Rudy et al.

(10) Patent No.: US 7,983,743 B2
(45) Date of Patent: Jul. 19, 2011

(54) SYSTEM AND METHOD FOR NONINVASIVE ELECTROCARDIOGRAPHIC IMAGING (ECGI)

(75) Inventors: Yoram Rudy, St. Louis, MO (US); Yong Wang, St. Louis, MO (US); Ping Jia, Solon, OH (US)

(73) Assignees: Case Western Reserve University, Cleveland, OH (US); Washington University, St. Louis, MO (US)

( * ) Notice: Subject to any disclaimer, the term of this patent is extended or adjusted under 35 U.S.C. 154(b) by 619 days.

(21) Appl. No.: 11/996,441

(22) PCT Filed: Jul. 21, 2006

(86) PCT No.: PCT/US2006/028287
§ 371 (c)(1),
(2), (4) Date: Jan. 22, 2008

(87) PCT Pub. No.: WO2007/013994
PCT Pub. Date: Feb. 1, 2007

(65) Prior Publication Data
US 2008/0213128 A1 Sep. 4, 2008
US 2009/0053102 A2 Feb. 26, 2009

Related U.S. Application Data

(60) Provisional application No. 60/701,626, filed on Jul. 22, 2005.

(51) Int. Cl.
*A61B 5/04* (2006.01)
(52) U.S. Cl. ........................... 600/509; 600/513
(58) Field of Classification Search .............. 600/509, 600/513, 523
See application file for complete search history.

(56) References Cited

U.S. PATENT DOCUMENTS

| | | | |
|---|---|---|---|
| 5,146,926 A | 9/1992 | Cohen | |
| 5,483,968 A | 1/1996 | Adam et al. | |
| 6,047,206 A | 4/2000 | Albrecht et al. | |
| 6,718,291 B1 * | 4/2004 | Shapiro et al. | 703/2 |
| 6,772,004 B2 | 8/2004 | Rudy | |
| 6,856,830 B2 | 2/2005 | He et al. | |
| 6,975,900 B2 | 12/2005 | Rudy et al. | |
| 7,016,719 B2 | 3/2006 | Rudy et al. | |
| 2002/0128565 A1 | 9/2002 | Rudy | |
| 2003/0120163 A1 * | 6/2003 | Rudy et al. | 600/509 |

OTHER PUBLICATIONS

A Meshless Method for Conjugate Heat Transfer Problems; Eivo et al.; Engineering Analysis with Boundary Elements 29 (2005) 136-149.*
H.S. Oster, B. Taccardi, R.L. Lux, P.R. Ershier, Y. Rudy, "Noninvasive Electrocardiographic Imaging: Reconstruction of Epicardial Potentials, Electrograms and Isochrones, and Localization of Single and Multiple Electrocardiac Events", Circulation 1997; 96: 1012-1024.

(Continued)

*Primary Examiner* — Carl H Layno
*Assistant Examiner* — Paula J Stice
(74) *Attorney, Agent, or Firm* — Tarolli, Sundheim, Covell & Tummino LLP

(57) ABSTRACT

Noninvasive systems and methods are provided for determining electrical activity for a heart of a living being. A processor is configured to meshlessly compute data that represents heart electrical activity from a set of noninvasively measured body surface electrical potentials. This is accomplished using data that describes a geometric relationship between a plurality of locations corresponding to where the body surface electrical potentials were measured and the heart.

37 Claims, 18 Drawing Sheets

OTHER PUBLICATIONS

J.E. Burnes, B. Taccardi, Y. Rudy, "A Noninvasive Imaging Modality for Cardiac Arrhythmias" Circulation Oct. 24, 2000; 102: 2152-2158.

C. Ramanathan, R.N. Ghanem, P. Jia, K. Ryu, Y. Rudy, "Electrocardiographic Imaging (ECGI): A Noninvasive Imaging Modality for Cardiac Electrophysiology and Arrhythmia" Nature Medicine, Mar. 2004; 10:422-428.

A. Eisenberg, Beyond the EKG, to a Hypersensitive heart monitor. New York Times. Apr. 22, 2004.

M.A. Goldberg and C.S. Chen, The Method of Fundamental Solutions for potential, Helmholtz and diffusion problems, in Boundary Integral Methods—Numerical and Mathematical Aspects, ed. M.A. Goldberg, Computational Mechanics Publications, 1998, pp. 103-176.

M.A. Goldberg, C.S. Chen & A.S. Muleshkov, The Method of Fundamental solutions for diffusion equations, Boundary Element Technology XIII, eds. C.S. Chen, C.A. Brebbia, D.W. Pepper, WIT Press, Boston, Southampton, pp. 377-386, 1999.

Y.C. Hon, T. Wei, A fundamental solution method for inverse heat conduction problems. Engineering Analysis with Boundary Elements, vol. 28, Issue 5, pp. 489-495, May 2004.

Y.C. Hon and T. Wei, The method of fundamental solution for solving multidimensional inverse heat conduction problems, *CMES-Comp. Model. Eng.* 7, 119-132 (2005).

Supplementary European Search Report for EP Application No. 06800185.8.

Fischer, G. et al., "*Application of high-order boundary elements to the electrocardiographic inverse problem*", Computer Methods and Programs in Biomedicine Elsevier Ireland, vol. 58, No. 2, (1999) pp. 119-131.

Karageorghis, Andreas and Fairweather, Graeme, "*The Method of Fundamental Solutions for the Numerical Solution of the Biharmonic Equation*", Journal of Computation Physics, London, GB, vol. 69, No. 2, Apr. 1, 1987, pp. 434-459.

Seger, M. et al., "*Lead Field Computation for the Eletrocardiographic inverse problem—finite elements versus boundary elements*", Computer Methods and Programs in Biomedicine Elsevier Amsterdam, NL, vol. 77, No. 3, Mar. 1, 2005, pp. 241-252.

* cited by examiner

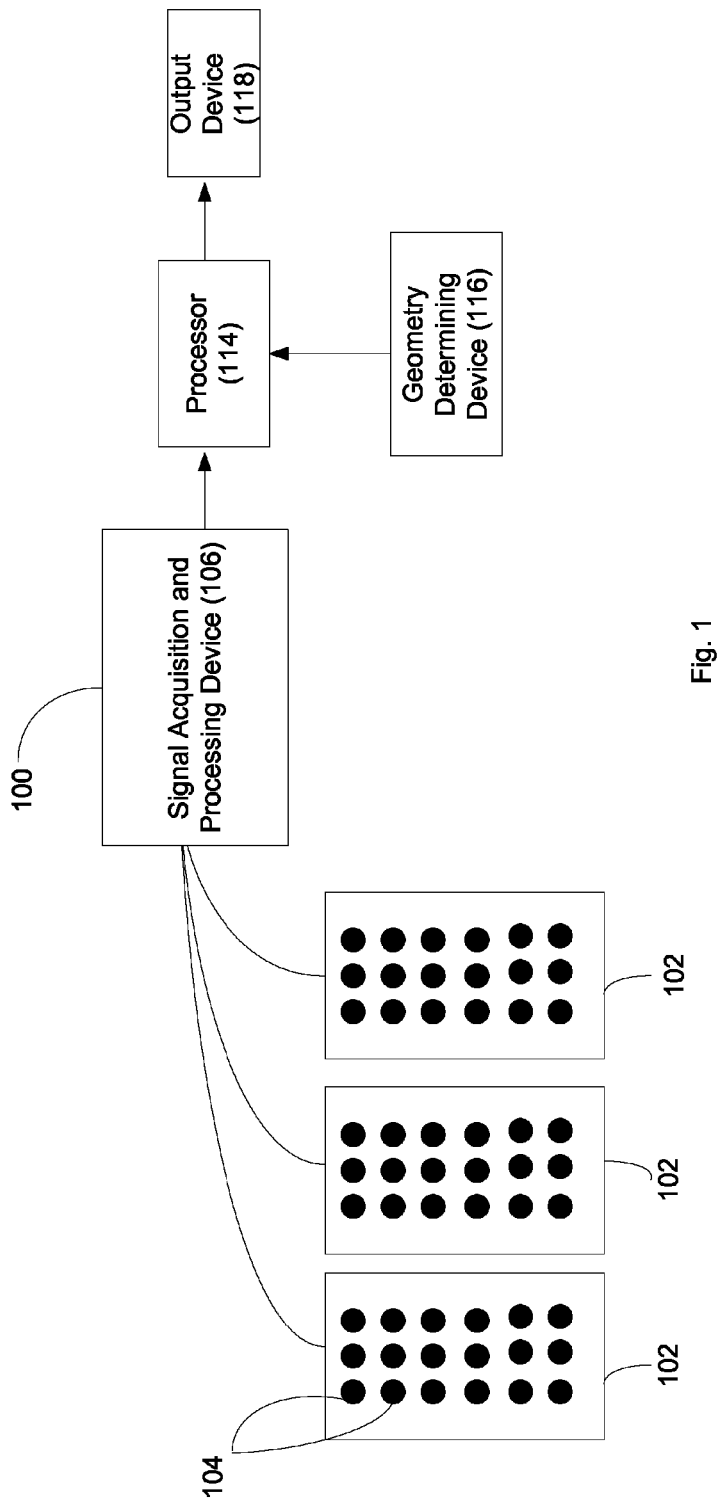

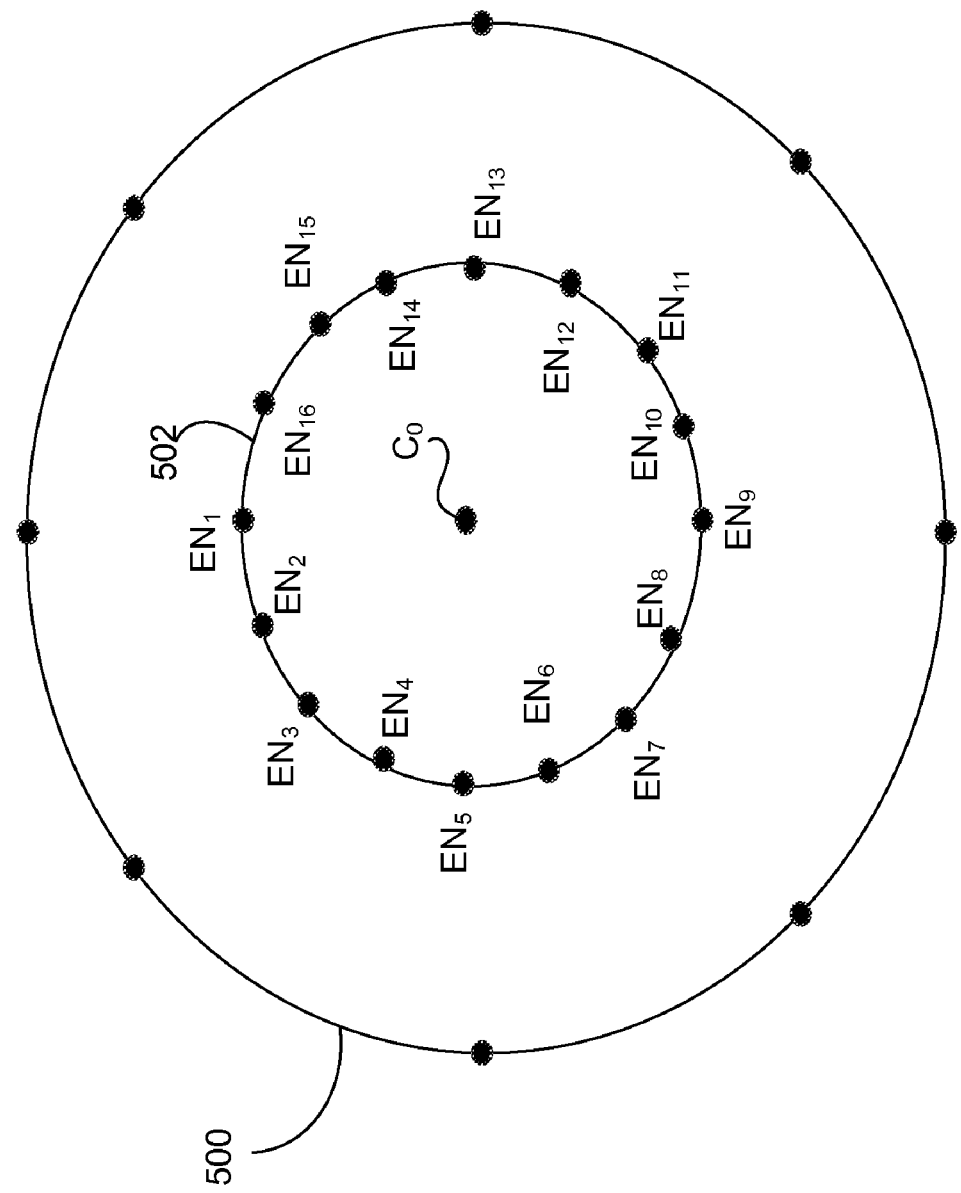

Figs. 10A-D

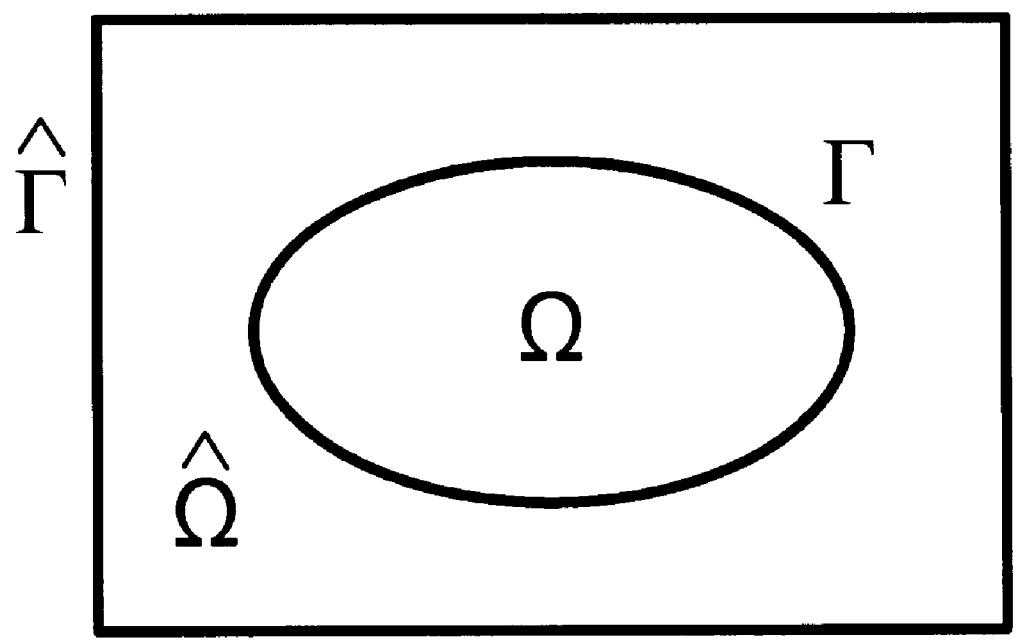
Fig. 15 (Appendix A)

SYSTEM AND METHOD FOR NONINVASIVE ELECTROCARDIOGRAPHIC IMAGING (ECGI)

RELATED APPLICATION

The present application claims priority to U.S. Provisional Application No. 60/701,626 file Jul. 22, 2005, which is incorporated herein by reference in its entirety.

STATEMENT REGARDING FEDERALLY SPONSORED RESEARCH OR DEVELOPMENT

This invention was made with government support under NIH-NHLBI Grant R37-HL-33343 awarded by the National Institutes of Health (NIH). The government may have certain rights in the invention

FIELD OF THE INVENTION

This invention relates to an improved technique for noninvasive electrocardiographic imaging (ECGI). In particular, the preferred embodiment of the present invention relates to a meshless noninvasive ECGI technique wherein a plurality of body surface potentials are noninvasively obtained and combined with data representing the geometry of a heart and body torso to generate electrocardiographic images that represent electrical activity of the heart.

BACKGROUND OF THE INVENTION

Over 7 million people worldwide (around 400,000 in the U.S.) die annually from rhythm disorders of the heart. Many more people are disabled each year from such rhythm disorders. Despite these alarming statistics, the development of a noninvasive imaging modality for cardiac arrhythmias to help physicians identify patients at risk of sudden death, provide specific diagnoses, and guide therapy has only recently borne fruit.

Previous works by one of the inventors herein in the field of noninvasive ECGI are represented by U.S. Pat. No. 6,772,004, entitled "System and Method for Non-Invasive Electrocardiographic Imaging" pending U.S. patent application Ser. No. 10/264,572, filed Oct. 4, 2002, entitled "System and Methods for Noninvasive Electrocardiographic Imaging (ECGI) Using Generalized Minimum Residual (GMRES)" now U.S. Pat. No. 7,016,719), and pending U.S. patent application Ser. No. 10/317,953, filed Dec. 12, 2002, entitled "Systems and Methods for Determining a Surface Geometry" now U.S. Pat. No. 6,975,900), the entire disclosures of all of which are incorporated herein by reference. These works disclose the computation of epicardial cardiac surface potentials, electrograms, and isochrones from noninvasively-measured body surface potentials using, in part, a technique known as the Boundary Element Method (BEM). For ease of reference, the technology disclosed in these applications will be referred to as BEM ECGI hereinafter. With BEM ECGI, 3D surface meshes of a patient's torso surface and epicardial cardiac surface are created to compute a matrix of coefficients A for translating measured body surface potentials to epicardial cardiac surface potentials (which in turn can be translated into electrograms and/or isochrones). This 3D surface meshing is an iterative time-consuming task that requires large memory resources. The BEM ECGI process is further slowed by the manual optimization of the surface meshes that is generally required to maintain accuracy in reconstructing the epicardial cardiac surface potentials. Meshing generally involves the definition of triangular-shaped elements (or elements of other shapes) that together define a 3D boundary around a surface of interest. Software can be used to initially automatically create the 3D surface mesh. However, this initial mesh will often need to be optimized to improve its accuracy, thereby further adding to the time required to accurately reconstruct the surface potentials and, in turn, further detracting from BEM ECGI's applicability to clinical applications. Moreover, the skill level required to optimize body surface and heart surface meshes is generally high, which limits the pool of people who are qualified to conduct BEM ECGI. Further still, even with a skilled person performing mesh optimization, it is believed by the inventors herein that BEM meshes nevertheless exhibit difficulty in accommodating complex heart geometries (particularly concave geometries) such as those that may be found in patients suffering from heart disease.

SUMMARY

Toward this end, the inventors herein have developed an ECGI system that employs a meshless algorithm to reconstruct heart surface electrical potentials from noninvasively measured body surface electrical potentials and data describing the geometrical relationship between the locations where the body surface potentials were measured and the heart surface. This meshless algorithm operates to translate electrical potentials measured at a plurality of locations along a body surface to any surface of interest that is defined between the epicardial cardiac surface and the body surface. Preferably, the surface of interest to which the body surface electrical potentials are translated is the epicardial cardiac surface. However, a practitioner of the present invention may choose to translate the body surface electrical potentials to any arbitrary surface between the epicardial cardiac surface and the body surface. Accordingly, the term "epicardial envelope" as used herein refers to any surface on or outside the epicardial cardiac surface and inside the volume defined by the body surface that at least partially encloses the epicardial cardiac surface. While the term "epicardial envelope" encompasses the actual outer surface of the epicardium, the term "epicardial cardiac surface" as used herein refers specifically to the actual outer surface of the epicardium.

In the most preferred embodiment, this meshless algorithm is the method of fundamental solution (MFS). As such, the preferred embodiment of the present invention will often be referred to herein as MFS ECGI.

Rather than employing a surface mesh of the body surface and heart surface, MFS ECGI operates to define a plurality of virtual source nodes both outside the body surface and inside the heart surface. The virtual source nodes that are located outside the body surface define a surface boundary outside the body surface. The virtual source nodes that are located inside the heart surface define a surface boundary inside the heart surface. Based on the known geometrical relationships between the virtual source nodes, the electrode positions where the body surface potentials are measured, and the epicardial nodes for which the heart surface electrical potentials are computed, the MFS technique can readily reconstruct the epicardial cardiac surface potentials from the measured body surface potentials.

Experimentation has shown that this MFS ECGI technique operates at speeds that are of orders of magnitude faster than BEM ECGI, all while consuming less memory resources and being amenable to implementation via relatively short software code. Further still, the inventors herein believe that this increase in speed and efficiency has not hindered accuracy. In fact, experimentation has shown that MFS ECGI is at least as accurate as and in some cases of higher accuracy than BEM ECGI.

The inventors herein believe that the improved performance of MFS ECGI relative to BEM ECGI opens wide new windows of opportunity for noninvasive ECGI, particularly in connection with medical applications where time is of the essence such as interventional medical applications (including but not limited to ablation of arrhythmia substrates, targeted drug delivery, lead placement for implanted devices such as pacemakers and implanted cardioverters/defibrillators (ICDs), and other surgical procedures), guidance of interventional medical applications, evaluation of drug effect, risk stratification, and exercise stress tests. Even in less time critical applications, the inventors herein believe that the present invention will dramatically improve turnaround time for ECGI such that results can be obtained in minutes rather than hours, even while the patient remains in the cardiac electrophysiology laboratory, thereby allowing for rapid diagnosis and possible ECGI-guided intervention.

Moreover, because of the reduced complexity and increased automation of MFS ECGI relative to BEM ECGI, it is believed by the inventors herein that the amount of training required by a user (such as a physician, fellow, or medical assistant) can be greatly reduced, thereby allowing for wider use in the field These and other features and advantages of the present invention are set forth below and in the enclosed figures.

BRIEF DESCRIPTION OF THE DRAWINGS

FIG. 1 illustrates a block diagram overview of a preferred system for meshless noninvasive ECGI;

FIGS. 2(a) and 2(b) depict exemplary geometry determining devices;

FIGS. 5(a)-(e) depict how source nodes can be configured during the preferred meshless noninvasive ECGI process;

FIG. 15 depicts an example of boundary conditions, which is part of Appendix A, for use in demonstrating a method of fundamental solution.

DETAILED DESCRIPTION OF THE PREFERRED EMBODIMENT

Figure 3:
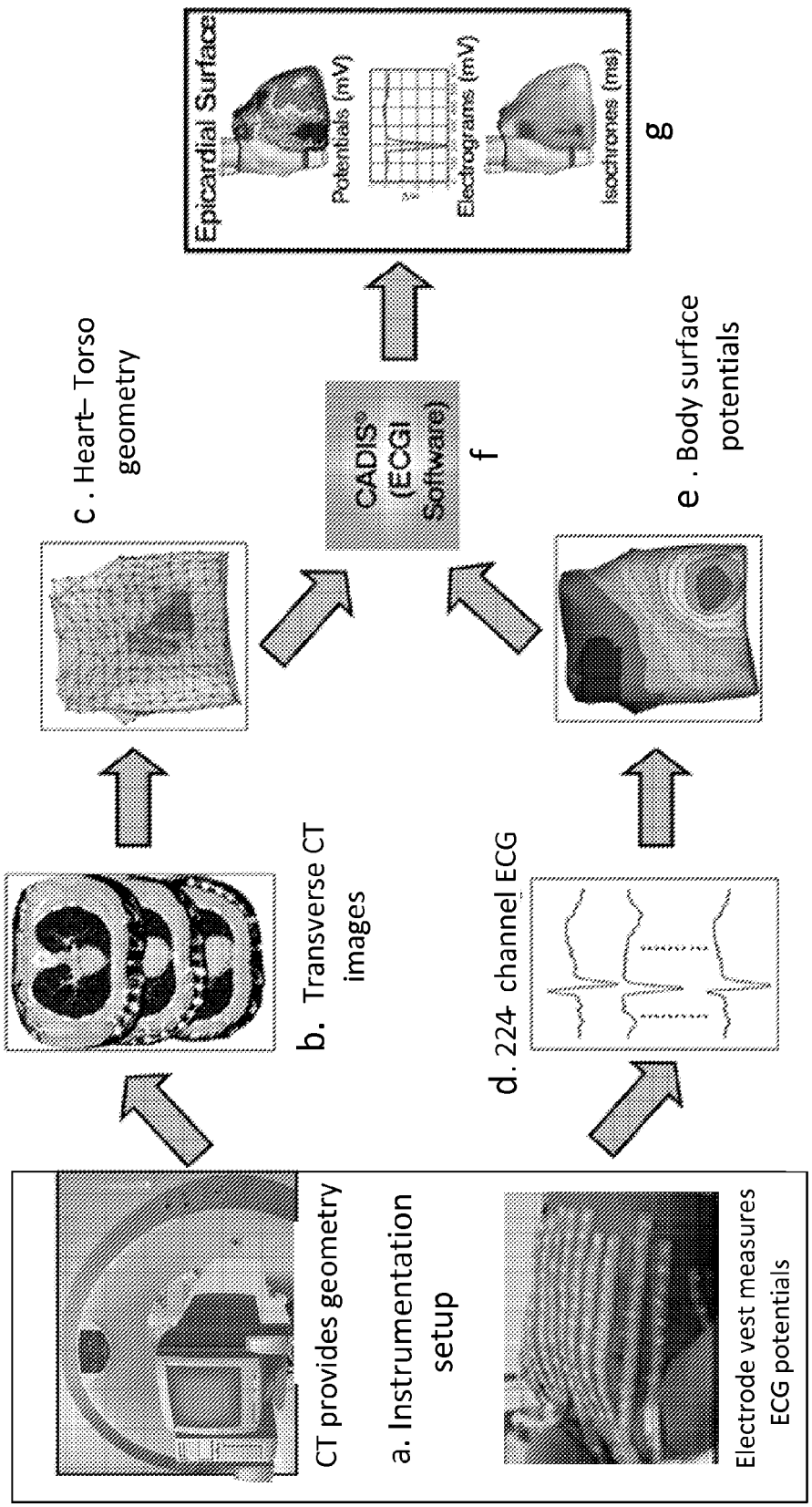
FIG. 3 depicts an exemplary high level flowchart for performing noninvasive ECGI.

FIG. 1 depicts a block diagram overview of a preferred system 100 for performing meshless noninvasive ECGI. The system 100 preferably comprises a plurality of electrodes 104 (mounted on strips 102, a vest, or in some other array) in communication with a signal acquisition and processing device 106. The electrodes 104 serve to sense a plurality of electrical potentials on a patient's body surface. The signal acquisition and processing device 106 operates to process this sensed data to a form suitable for digital processing, as is known in the art. The system 100 also comprises a geometry determining device 116 that serves to generate data that is indicative of the geometrical relationship between the electrodes 104 and one or more points of interest within the patient (e.g., the patient's epicardial cardiac surface).

Processor 114 operates to (1) receive data from both the electrodes 104 (by way of the signal acquisition and processing device 106) and the geometry determining device 116 and (2) reconstruct epicardial cardiac surface potentials from the received data. The reconstructed epicardial potentials can then be used to provide, via the output device 118, electrograms, isochrones (activation maps), epicardial cardiac potential maps, or other data representations derived from the epicardial potentials (e.g., integral maps, recovery maps, activation-recovery interval maps, etc.). An example of a suitable processor 114 for the present invention is a conventional desktop or laptop computer, such as a 2.4 GHz laptop computer with a gigabyte of RAM. However, as would be understood by those having ordinary skill in the art, any processor with sufficient memory resources and computational speed would be suitable for use as processor 114. Output device 118 may be any device capable of effectively communicating the results of the reconstruction to a user, such as a display monitor and/or printer associated with the processor 114, as would be understood by those having ordinary skill in the art.

It is also worth noting that a variety of known techniques for electronic data communication can be used as the data links between the various elements depicted in FIG. 1, as would be understood by those of ordinary skill in the art. Furthermore, it should be understood that the meshless ECGI technique described herein can readily be implemented in software and/or hardware for execution by one or more processors to compute epicardial cardiac surface potentials. Moreover, in some instances the processor 114 and geometry determining device may be integrated into the same platform, such as a CT scanner, an MRI scanner, a bi-plane X-ray fluoroscopy apparatus, or an ultrasound echocardiography apparatus that has MFS ECGI processing capabilities built-in.

Electrodes 104 are preferably arranged on a plurality of strips 102 that can be placed in position on the torso of a patient undergoing ECGI. Alternatively, a vest arrangement as shown in U.S. Pat. No. 6,772,004 and U.S. Pat. No. 7,016,719 may also be used. As mentioned above, electrodes 104 measure the electrical potentials on the patient's torso. The electrodes 104 that are used are preferably electrodes that are visible in the imaging modality used by the geometry determining device 116. Otherwise, it is preferred that appropriate markers be placed on the electrodes to render them visible in the images produced by the geometry determining device 116. When practicing the present invention, the total number of electrodes 104, the number of electrodes 104 per strip 102, the number of electrode strips 102, and the placement of the electrode strips 102 on the patient can be variable according to the needs of a practitioner of the present invention. However, it is preferred that as much of the patient's torso (front, back, and sides) be covered by electrodes 104 as possible. For example, the total number N of electrodes 104 could range from 120 to 250. However, the value of N may be more or less than a value within this range, as would be understood by a person having ordinary skill in the art. However, the inventors herein believe that the use of too few electrodes will reduce the accuracy of the reconstructed epicardial cardiac surface potentials.

The electrodes can be wet electrodes or dry electrodes, as would be understood by those having ordinary skill in the art. By avoiding the use of gels, short circuiting risks arising from a high concentration of electrodes can be reduced. An example of a suitable type of electrode to obtain body surface potentials is a silver/silver chloride (Ag/AgCl) electrode. However, other types of electrodes such as carbon electrodes can also be used. However, if CT is used as the imaging modality for the geometry determining device, then it is preferred that CT markers be disposed on the carbon electrodes to render them visible in the CT images.

The signal acquisition and processing device 106 is preferably a multi-channel device that operates to receive the sensed electrical potentials from the electrodes 104, process that data, and supply it to processor 114. Practitioners of the present invention may select a commercially-available system to use as the signal acquisition and processing device 106. For example, the Active Two system that is available from BioSemi of WG-Plein 129, 10545C, Amsterdam, Netherlands, which is a 256-channel, DC amplifier, 24 bit resolution biopotential measurement system, may serve as device 106. The Active Two biopotential measurement system includes an analog-to-digital converter (ADC) that receives electrode data from electrodes 104, a power source (battery and charger), a USB2 receiver that receives the digital output from the ADC via a fiber optic connection and provides the digital electrode data to acquisition software resident on processor 114 via a USB2 connection. The analog input box that is also part of the Active Two system may be omitted from the practice of the preferred embodiment.

It should also be noted that custom-designed signal acquisition and processing device 106 can also be used, such as the one described in prior U.S. Pat. No. 6,772,004 and U.S. Pat. No. 7,016,719.

The geometry determining device 116 may take a variety of forms, as described in prior U.S. Pat. Nos. 6,772,004, 7,016,719 and 6,975,900, including x-ray, ultrasound, computed tomography (CT) and magnetic resonance imaging (MRI). For example, as shown in FIG. 2(a), the geometry determining device 116 may take the form of a CT scanner or MRI device 200. The operation and collection of data therefrom will be apparent to those of ordinary skill in the art. In one embodiment, the CT scanner/MRI device 200 is used to generate data, or images, to determine torso geometry and, consequently, body surface electrode positions as well as an epicardial envelope surrounding the heart. As those of skill in the art will appreciate, the epicardial envelope is a suitable estimate of the epicardial cardiac surface itself, which could also be determined. It should also be recognized that locating the epicardial envelope or surface necessarily involves location of the heart. As a further example, as shown in FIG. 2(b) and described in greater detail in prior U.S. Pat. Nos. 6,772,004, 7,016,719 and 6,975,900, the geometry determining device 116 may also take the form of a bi-plane x-ray machine 202 and a digitizer 204.

FIG. 3 depicts a high level view of the noninvasive ECGI process. After appropriately applying electrode strips 102 (or vest) to the patient's torso and after appropriately setting up a geometry determining device 116 such as a CT scanner (step a), (1) a plurality of ECG potentials on the patient's torso can be measured via the electrodes (step d), (2) these measured ECG potentials can be processed to generate body surface potential data (step e), (3) a plurality of transverse CT images of the patient's torso can be obtained, and (4) these CT images can be processed to determine the patient's 3D heart-torso geometry (step c). At step f, the software components of the preferred embodiment preferably operate to combine and process the body surface potential data and the heart-torso geometry data to reconstruct estimates of the epicardial cardiac surface potentials. These reconstructed epicardial cardiac surface potentials can in turn be processed at step g to generate appropriate epicardial cardiac surface potential maps, epicardial cardiac surface electrograms, and epicardial cardiac surface isochrones.

Figure 4:
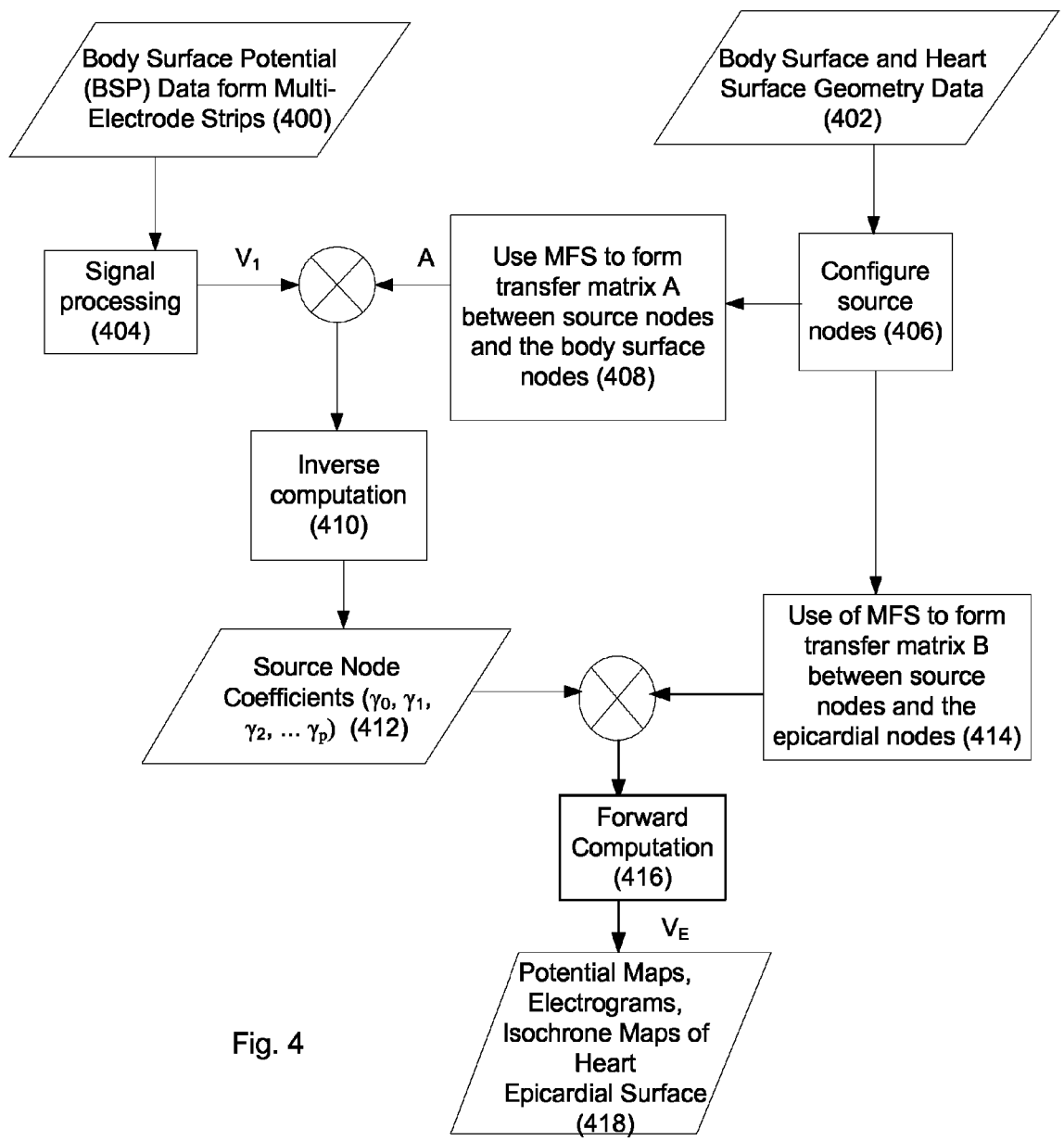
FIG. 4 is an exemplary flowchart for performing meshless noninvasive ECGI.

FIG. 4 depicts the preferred flow for the meshless noninvasive ECGI of the present invention in greater detail. Signal acquisition and processing as described in connection with device 106 is performed on the sensed body surface potential data 400 from electrodes 104 to generate a 1xN vector $V_T$ of torso surface potentials, wherein N preferably represents the total number of electrodes 104 used by system 100 such that $V_T(i)$ represents the torso surface potential that was measured by a particular electrode 104(i). $V_T$ serves as a body surface potential map (BPSM). It is desired to reconstruct an epicardial cardiac surface potential map $Y_E$ from $V_T$ using geometry data 402 that identifies the geometrical relationship between the torso surface, torso electrodes, and epicardial cardiac surface. This geometry data can be obtained from geometry determining device 116 as described in connection with FIGS. 1 and 2. It should be recognized that in a clinical setting, the geometry data 402 would be generated by the geometry determining device 116; however, it should also be noted that when executing the MFS ECGI technique for testing and/or validation purposes, the geometry data 402 may be known parameters, such as those associated with geometric spheres and torso tanks (used in testing), that are simply input to the system.

Returning to a clinical example, the geometry data can be a plurality of CT slices from which the patient's torso surface, the torso electrodes disposed on the patient's torso surface, and epicardial cardiac surface can be identified. Furthermore, based on the known slice thickness and scan parameters, the location of any given point on each slice can be determined in a three-dimensional (3D) coordinate space, and thus the geometrical relationship between any two points can also be determined in the 3D coordinate space.

Figure 5A:
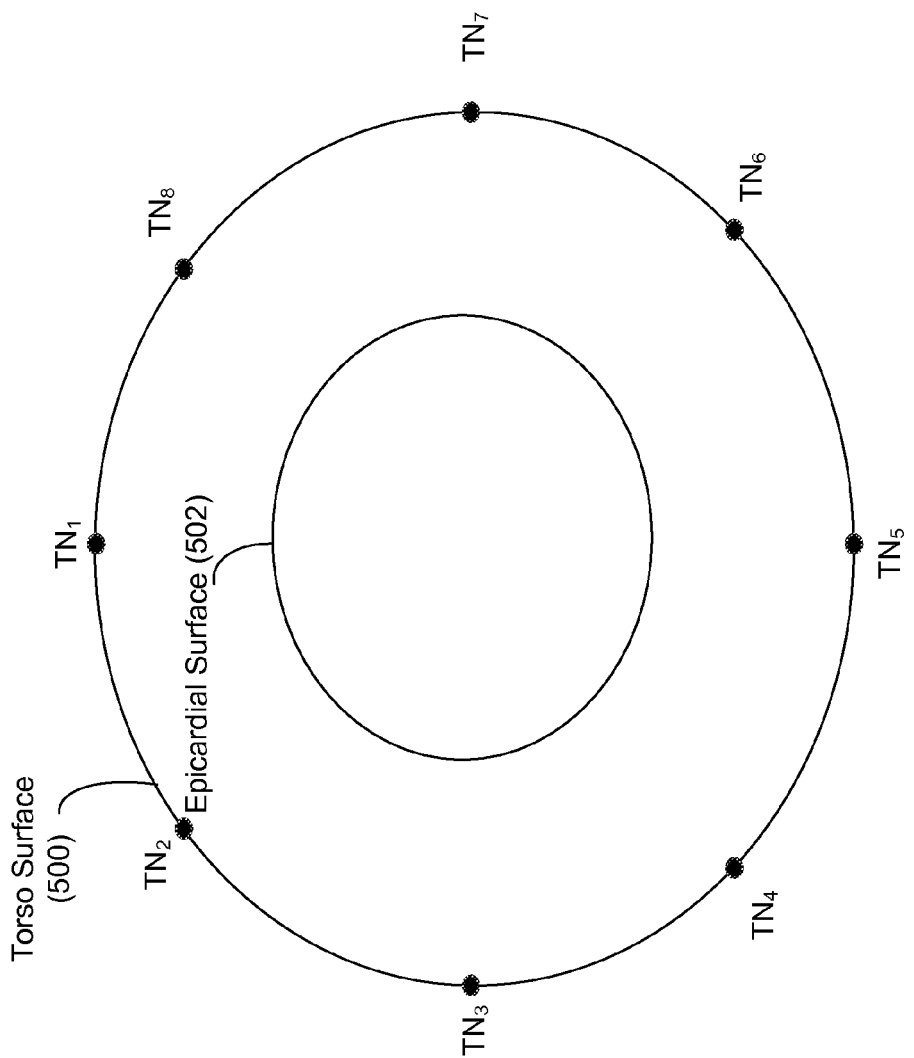

FIG. 5(a) depicts an exemplary CT scan in which the patient's torso surface 500 and epicardial cardiac surface 502 are visible. For the purposes of explaining the meshless technique referred to herein as the Method of Fundamental Solution (MFS), a two-dimensional (2D) example will be given. However, it should be understood by those having ordinary skill in the art that the MFS technique can be readily extended to three dimensions for use in real world applications. Further, it should be understood that the surfaces and node locations depicted in FIGS. 5(a)-(e) are exemplary only and are not drawn to scale.

Visible in the image of FIG. 5(a) are N torso electrodes (or torso nodes) $TN_1$ through $TN_N$. As can be seen from FIG.

5(a), in this example, N equals 8. However, it should be understood this value of N is exemplary only and chosen for simplicity in connection with explaining the principles of the preferred embodiment of the present invention. As previously explained, in practice, it is preferred that much larger values of N be used.

Each torso node $TN_i$ corresponds to the location where an electrical potential of the patient's torso surface 500 has been measured. The goal of the preferred embodiment is to translate the potential measurements at the torso nodes to nodes located on the epicardial envelope. In a most preferred embodiment, the torso node measurements are translated to nodes on the epicardial cardiac surface 502. To perform this translation to the epicardial cardiac surface, the locations of the nodes on the epicardial cardiac surface 502 (referred to herein as "epicardial nodes"—wherein "epicardial nodes" refers to the nodes that are defined on the epicardial cardiac surface specifically or on the epicardial envelope) should first be determined.

As part of this process, FIG. 5(b) depicts a plurality of epicardial nodes that are located on the patient's epicardial cardiac surface 502. If the torso node measurements are being translated to nodes on the epicardial envelope other than the epicardial cardiac surface 502, then the epicardial nodes will be located on the particular surface of interest. Because the heart is clearly visible in the CT slices, any of a variety of techniques can be used to identify the epicardial cardiac surface 502. For example, commercially-available or custom-designed medical image visualization and segmentation software, such as the well-known Amira 3D visualization software package, can be used to identify, segment, and label the heart and heart surface 502 in the CT slices. Segmentation can be performed manually or automatically by known algorithms in the art. To appropriately place each epicardial node (EN), either a manual or automatic technique can be used to place a plurality M of ENs on the epicardial cardiac surface 502. With a manual technique, a user manually places the ENs at user-selected points along the epicardial cardiac surface 502. With an automated technique, an algorithm automatically distributes the ENs along the epicardial cardiac surface 502. It is worth noting that accuracy in node placement is important because any error in determining node position can cause computational error during the inverse computation described below. The value of M can vary as a design choice by a practitioner of the present invention. However, it is preferred that a sufficient number of ENs be placed on surface 502 such that the MFS technique described herein exhibits a desired degree of resolution. An example of a suitable value for M is 100 or more. Preferably, these M ENs are evenly distributed over the epicardial cardiac surface 502, but this need not be the case. For example, in some instances it may be desirable to obtain high spatial resolution reconstruction in a certain area of the heart, in which case a practitioner of the present invention may choose to concentrate more ENs in that area than in other areas.

Next, at step 406, a plurality of source nodes are configured. These source nodes are "virtual" nodes that are placed to define two surfaces—one that is outside the torso surface 500 and one that is inside the epicardial cardiac surface 502. The shape of each of these surfaces can be arbitrary so long as the outer surface remains outside the torso surface 500 and the inner surface remains inside the epicardial cardiac surface 502. Two general approaches may be used when configuring the source nodes: (1) a static configuration where the source nodes that define the fictitious boundaries are placed at fixed and pre-selected locations, and (2) a dynamic configuration where the locations of the source nodes that define the fictitious boundaries are determined dynamically by a complex nonlinear optimization procedure. Because of the complex and time-consuming nature of the nonlinear optimization procedure, dynamic configuration of source nodes is not preferred. Instead, it is preferred that a static configuration be used.

With a static configuration of source nodes, several configuration options are available when practicing the present invention, as would be understood by those having ordinary skill in the art. A preferred static configuration technique is a technique wherein the source nodes are placed at locations parallel to the torso surface (some distance outward therefrom) and epicardial cardiac surface (some distance inward therefrom). With this technique, the source nodes are defined such that (1) the outer surface source nodes are placed some fixed distance outward from each torso node along the rays extending from $C_0$ through each of the torso nodes, and (2) the inner surface source nodes are placed some fixed distance inward from each epicardial node along the rays extending from $C_0$ through each of the epicardial nodes, wherein $C_0$ represents the geometric center of the heart. $C_0$ can be readily determined by conventional segmentation software as previously described. The fixed distance that is used for source node placement can be variable as a design choice for a practitioner of the present invention. However, in one embodiment, a ratio of 1.2:1 can be used for configuring source nodes from the torso nodes and a ratio of 0.8:1 can be used for configuring source nodes for the epicardial nodes. In this example (wherein each source node that defines the fictitious surface outside the torso surface is inflated at a 1.2:1 ratio), if a given torso node was located 1 unit of measurement from $C_0$, then the source node corresponding to that torso node would be located along a ray extending from $C_0$ through that torso node at a location 1.2 units of measurement from $C_0$. Also with this example (wherein each source node that defines the fictitious surface inside the epicardial cardiac surface is deflated at a 0.8:1 ratio), if a given epicardial node was located 1 unit of measurement from $C_0$, then the source node corresponding to that epicardial node would be located along a ray extending from $C_0$ through that epicardial node at a location 0.8 units of measurement from $C_0$.

Figure 5C:
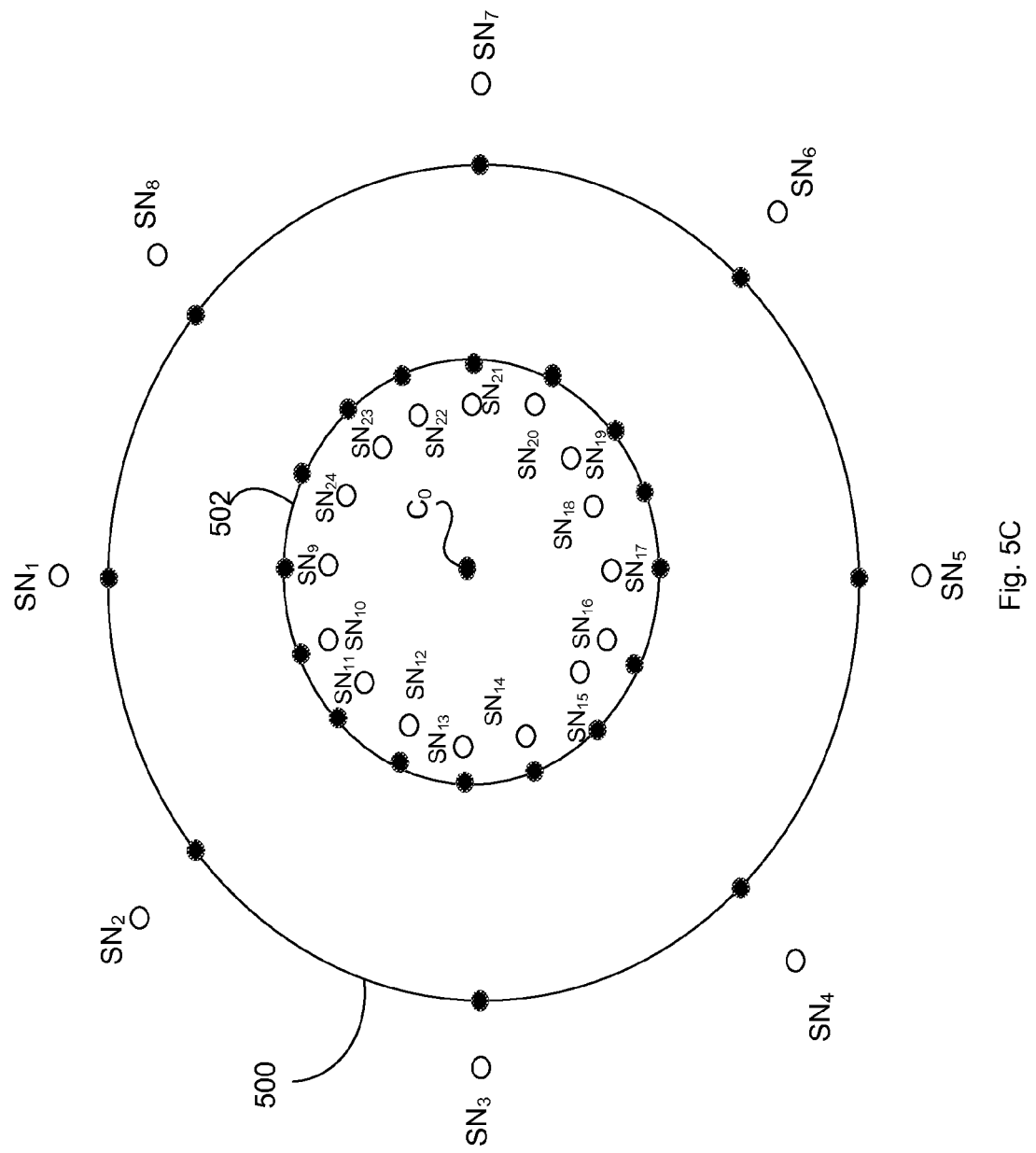

FIG. 5(c) depicts such a placement of source nodes $SN_1$ through $SN_{24}$. Continuing from the examples of FIGS. 5(a) and (b), wherein N TNs and M ENs have been defined, it can be seen that the total number P of source nodes will be N+M in the preferred embodiment. For this example, where N equals 8 and M equals 16, this means that P equals 24. However, this need not be the case, as the number of source nodes can be selected independently of the number of torso nodes and epicardial nodes. Source nodes $SN_1$ through $SN_8$ define an outer surface wherein $SN_1$ is some fixed distance outward from $TN_1$ along a ray extending from $C_0$ through $TN_1$, wherein $SN_2$ is that fixed distance outward from $TN_2$ along a ray extending from $C_0$ through $TN_2$, and so on. Source nodes $SN_9$ through $SN_{24}$ define an inner surface wherein $SN_9$ is some fixed distance inward from $EN_1$ along a ray extending from $C_0$ through $EN_1$, wherein $SN_{10}$ is that fixed distance inward from $EN_2$ along a ray extending from $C_0$ through $EN_{10}$, and so on. Furthermore, as would be understood by those having ordinary skill in the art, the coordinate values of each source node $SN_i$ in the 3D coordinate space of the patient's torso are known, thereby making distance determinations between (1) each source node and each torso node and (2) each source node and each epicardial node easy to calculate.

Figure 5D:
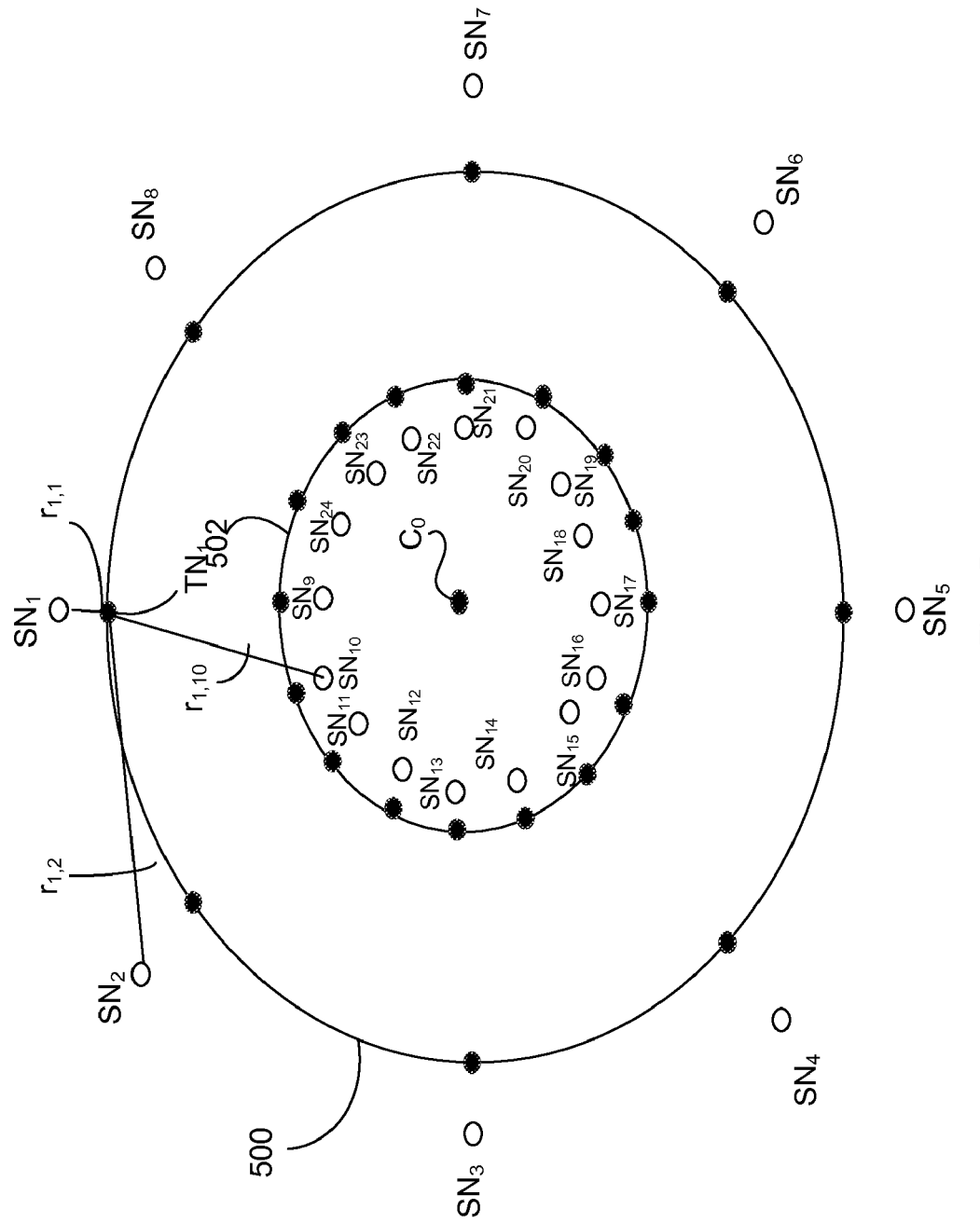
Figure 6:
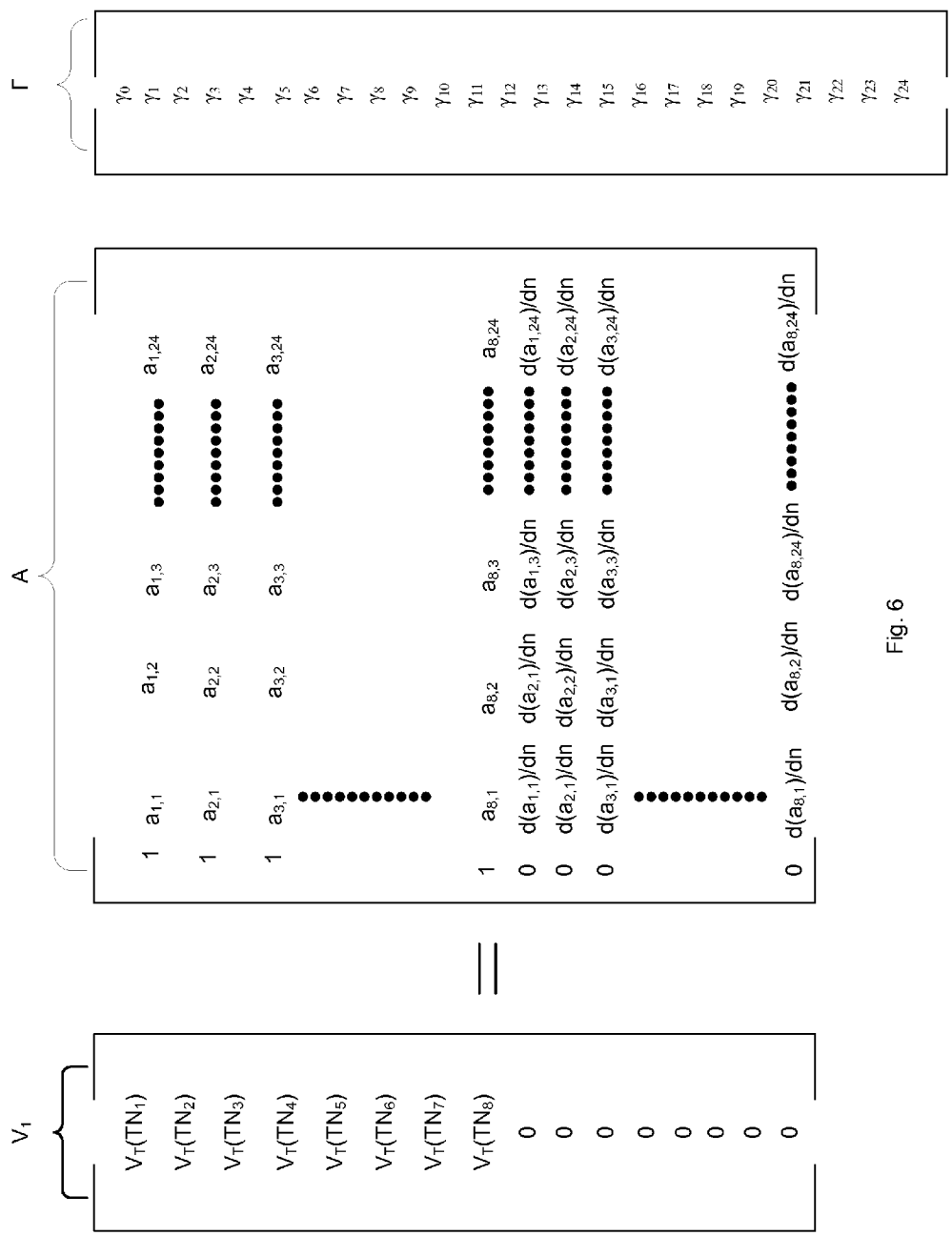
FIG. 6 depicts the matrix equation for relating torso surface potentials to source nodes.

At step 408, the process operates to determine a transfer matrix A that translates the measured torso potentials $V_T$ at each torso node to a plurality of source node coefficients, which reflect the "strength" of each source node, such that:

$$V_T = A\Gamma$$

wherein A is a 2N×P+1 matrix, wherein N represents the total number of torso nodes and wherein P represents the total number of source nodes. This equation is shown in greater detail in FIG. 6, wherein the vector $V_T$ is represented by the torso surface potentials at the various torso nodes for $V_T(1)$ through $V_T(N)$ and 0 (to represent the current) for $V_T(N+1)$ through $V_T(2N)$. The value of each entry $a_{j,k}$ in matrix A is a function of the distance between torso node $TN_j$ and source node $SN_k$, preferably such that:

$$a_{j,k} = \frac{1}{r_{j,k}}$$

wherein $r_{j,k}$ equals the distance between torso node $TN_j$ and source node $SN_k$. FIG. 5(d) depicts various distances r from torso node TN to exemplary source nodes (in this example, $SN_1$, $SN_2$, and $SN_{10}$). For ease of reference, FIG. 5(d) does not depict each distance r from each torso node to each source node, but a person having ordinary skill in the art would readily understand from FIG. 5(d) how each value of r would be determined.

Figure 5E:
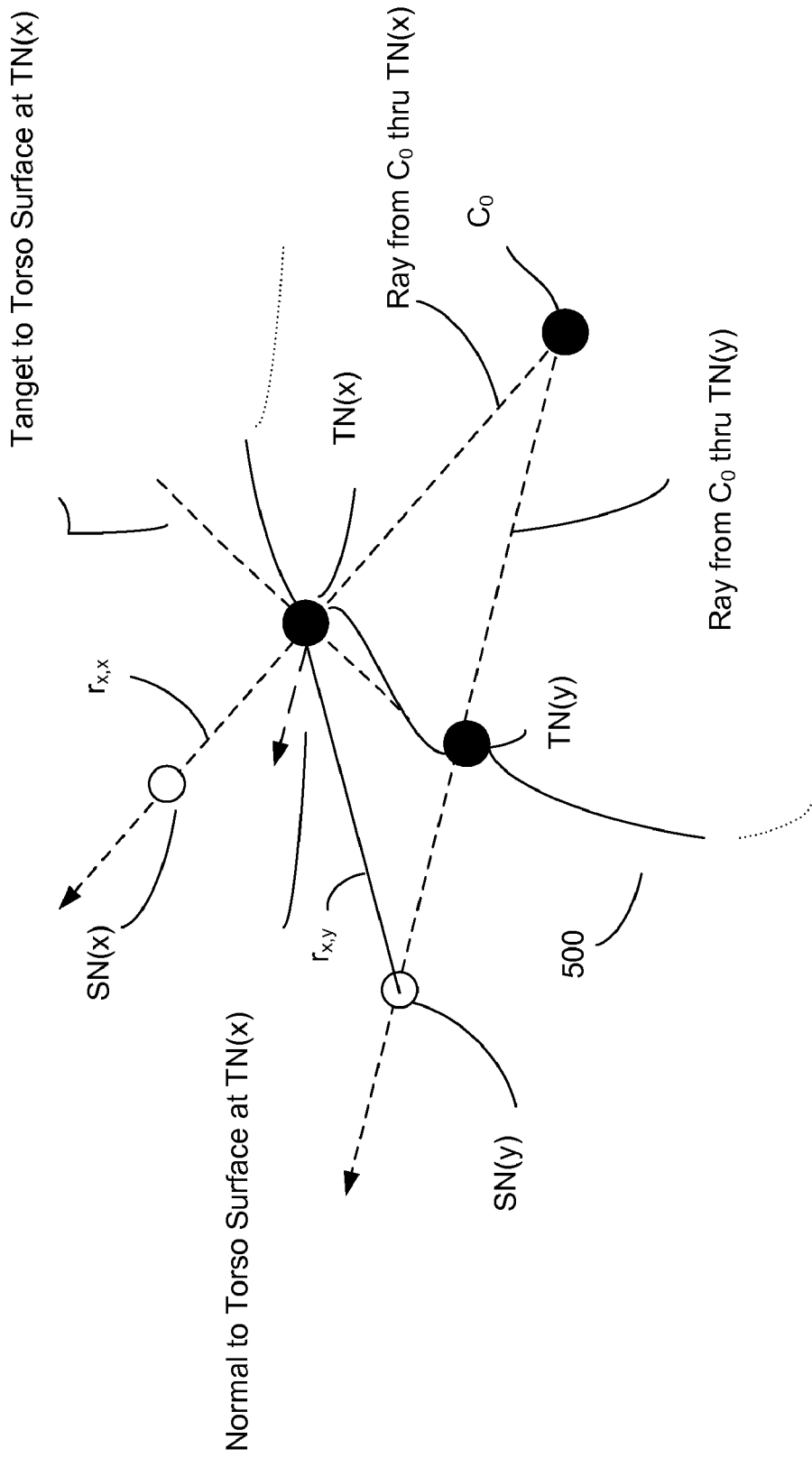

The values $d(a_{j,k})/dn$ in matrix A represent the derivatives of each $a_{j,k}$ term relative to the normal n defined by the torso surface 500 at the applicable torso node. FIG. 5(e) illustrates the relationship between $r_{j,k}$ and normal n for an exemplary torso node TN(x). The normal to the torso surface 500 at given torso node TN(x) is defined as the perpendicular to the torso surface tangent at that torso node TN(x). Thus, the $d(a_{x,k})/dn$ terms for the row in A corresponding to torso node TN(x) will be computed from the normal to the torso surface 500 at TN(x), as shown in FIG. 5(e).

Because each value for $r_{j,k}$ is readily calculable in view of the known coordinates of each torso node and each source node, the entries in matrix A are all known. Also, $V_T$ is known as its values are measured by the torso electrodes (and the zero terms for the current entries in the vector). Therefore, the 1×P+1 vector Γ is the only unknown. To find each value $\gamma_i$ in Γ, the inverse of A needs to be calculated at step 410, and wherein:

$$\Gamma = A^{-1}V_T$$

The computation of Γ is an ill-posed problem as small perturbations in the data (e.g., potential measurement noise and/or geometrical inaccuracy) can cause large unbounded errors. To reduce these potential errors, a variety of mathematical schemes that are known in the art can be used. Two schemes that are believed to provide effective results are Tikhonov zero order regularization and the Generalized Minimal Residual (GMRes) method. These techniques are described in U.S. Pat. No. 6,772,004 and U.S. Pat. No. 7,016,719, the entire disclosures of which have been incorporated herein by reference. By following the teachings of these references (wherein the variable $V_E$ as described in those references in connection with Tikhonov regularization and GMRes is replaced by Γ), a person having ordinary skill in the art can readily perform the inverse computation of step 410 to determine Γ (represented as source node coefficients 412 ($\gamma_0$ through $\gamma_P$) in FIG. 4).

Figure 7:
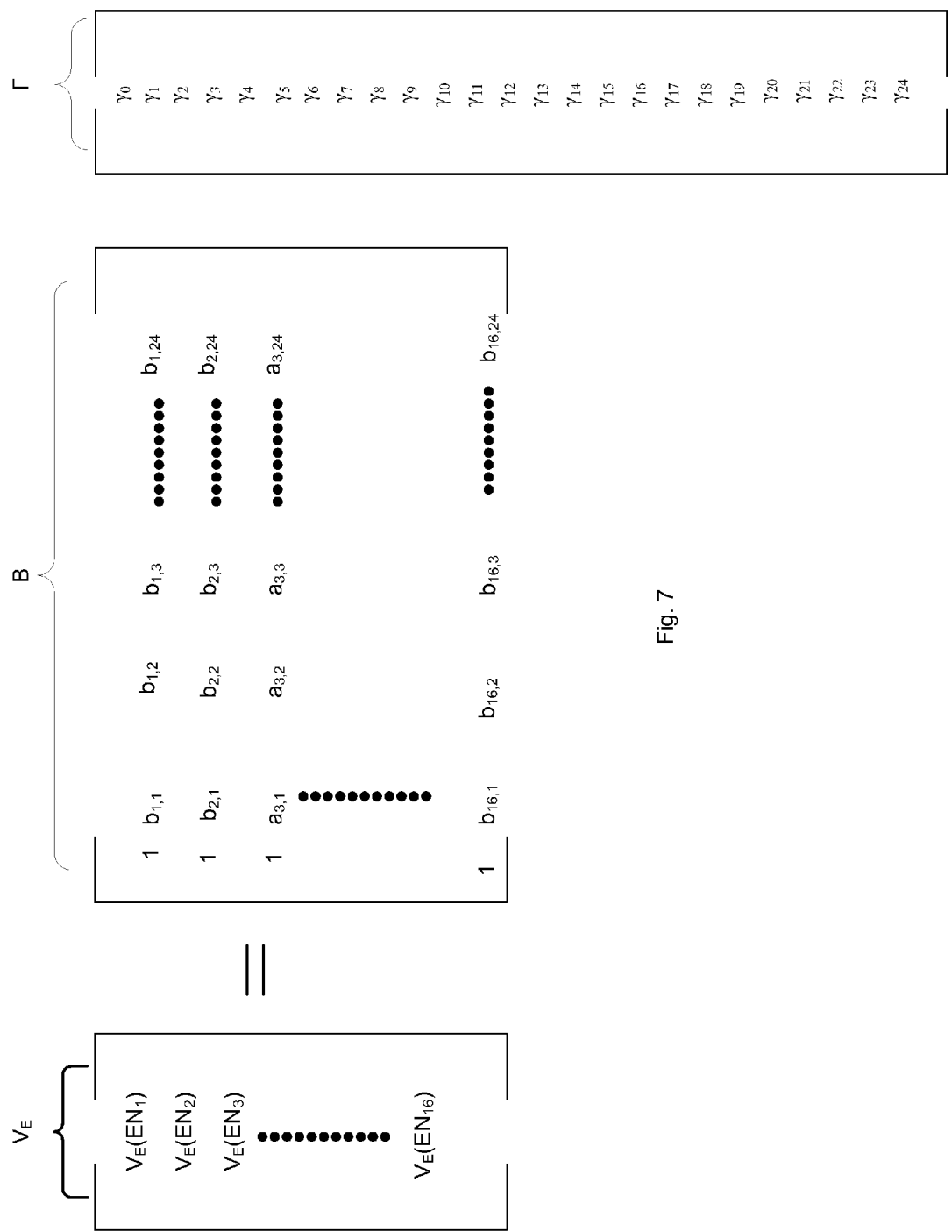
FIG. 7 depicts the matrix equation for relating source nodes to epicardial cardiac surface potentials.

Once Γ is known, a forward computation 416 can be used to determine the epicardial cardiac surface potentials $V_E$. To do so, at step 414, a transfer matrix B must first be computed. Matrix B operates to translate the source node coefficients $\gamma_0$ through $\gamma_P$ to epicardial cardiac surface potentials at each epicardial node $EN_1$ through $EN_M$ such that:

$$V_E = B\Gamma$$

wherein B is a M×P+1 matrix, wherein M represents the total number of epicardial nodes and wherein P represents the total number of source nodes. This equation is shown in greater detail in FIG. 7 which continues the example set forth in FIGS. 5 and 6. The value of each entry $b_{j,k}$ in matrix B is a function of the distance between epicardial node $EN_j$ and source node $SN_k$, preferably such that:

$$b_{j,k} = \frac{1}{r_{j,k}}$$

wherein $r_{j,k}$ equals the distance between epicardial node $EN_j$ and source node $SN_k$, which is the same principle shown in FIG. 5(d) albeit using epicardial nodes rather than torso nodes. As each value for $r_{j,k}$ is readily calculable, the entries in matrix B are all known, which allows for a straightforward calculation of $V_E$ from B and Γ.

Each entry $V_E(EN_i)$ within $V_E$ will represent an estimation of the epicardial cardiac surface potential at the location on the epicardium defined by $EN_i$. From $V_E$ (or from a plurality of $V_E$'s calculated from a plurality of successively measured $V_T$'s, as may be appropriate), persons having ordinary skill in the art can readily produce a variety of potential maps, electrograms, isochrone maps, recovery maps, integral maps, and activation-recovery interval maps of the patient's epicardial cardiac surface at step 418. As can be seen from the foregoing description, $V_E$ can be computed from $V_T$ without requiring a mesh of the torso or heart surfaces, thereby (among other advantages) greatly improving the speed of calculation for $V_E$. Additional details about the MFS technique are included herewith in Appendix A.

Experimental Results—Computational Speed:

The reconstructed epicardial cardiac surface potentials $V_E$ were verified using benchmark data derived from a human-shaped torso-tank, the details of which are described in U.S. Pat. No. 6,772,004. Additionally, data from experimentation using the torso tank allowed for comparisons to be made between the ECGI technique using MFS, the ECGI technique using BEM, and directly measured epicardial potentials.

Figure 8:
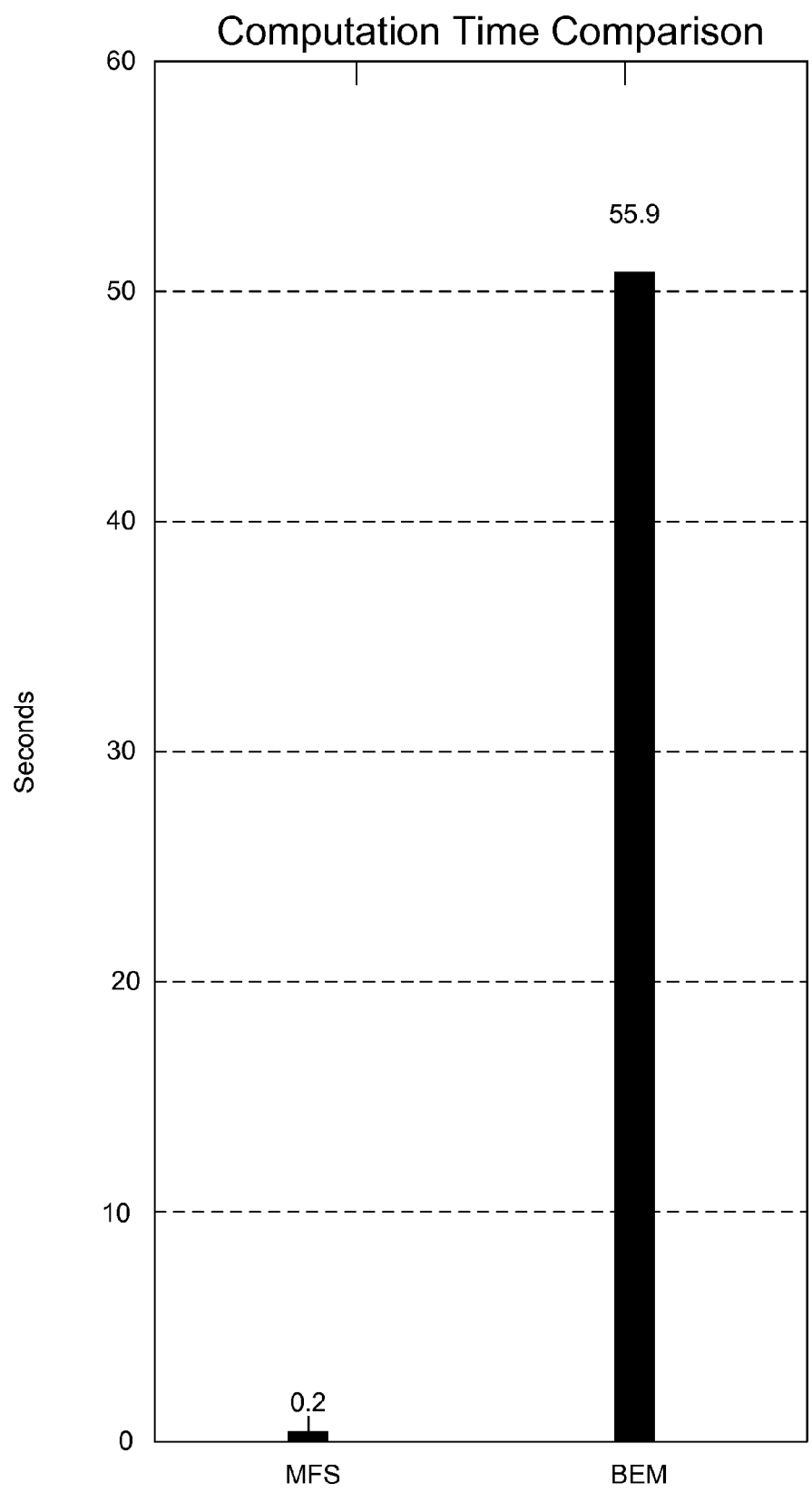
FIG. 8 is a chart comparing computation times for MFS ECGI versus BEM ECGI.

With respect to computation time, experimentation has shown that, using a laptop computer with a Pentium Mobile 1.7 GHz processor and 1G of RAM, BEM ECGI takes approximately 50.5 seconds to construct its transfer matrix A and achieve epicardial cardiac surface potential reconstruction for one time frame, while MFS ECGI in accordance with the teachings herein only takes about 0.2 seconds to form its transfer matrices A and B and achieve epicardial cardiac surface potential reconstruction for one time frame. The marked advantage in computation speed enjoyed by the MFS technique of the present invention over the prior BEM technique is shown in FIG. 8. Moreover, it is worth noting that this computation time comparison did not take into account the additional manual editing time that the prior BEM ECGI technique requires when the user optimizes the torso and heart meshes. As such, the meshless technique of the present invention is expected to exhibit an even greater computation time advantage over the BEM ECGI technique than that depicted in FIG. 8.

Further still, it is worth noting that in the comparison shown in FIG. 8, abundant RAM (1G) was provided. It can be expected that in real world clinical applications, the RAM will be shared with other programs on the same machine, in which case less RAM will be available to the ECGI process. Because the BEM ECGI technique consumes significantly more RAM resources than does the meshless ECGI technique (it is believed that the MFS technique's elimination of the need to generate and manipulate 3D surface meshes of the heart and torso may possibly provide at least 66% savings in consumed RAM resources), it is believed that the MFS ECGI technique can operate at high speeds (relative to BEM ECGI) even in the face of reduced RAM.

Experimental Results—Single Pacing:

Focal sites of initiation of arrhythmogenic activity can result from abnormal automaticity, triggered activity, or micro-reentry. Because the focus is usually confined to a small region of the myocardium, it can be simulated by pacing the myocardium at a single site. Locating the ectopic focus is important for activities such as diagnosis and guiding an interventional therapeutic procedure (e.g., ablation).

Figure 9:
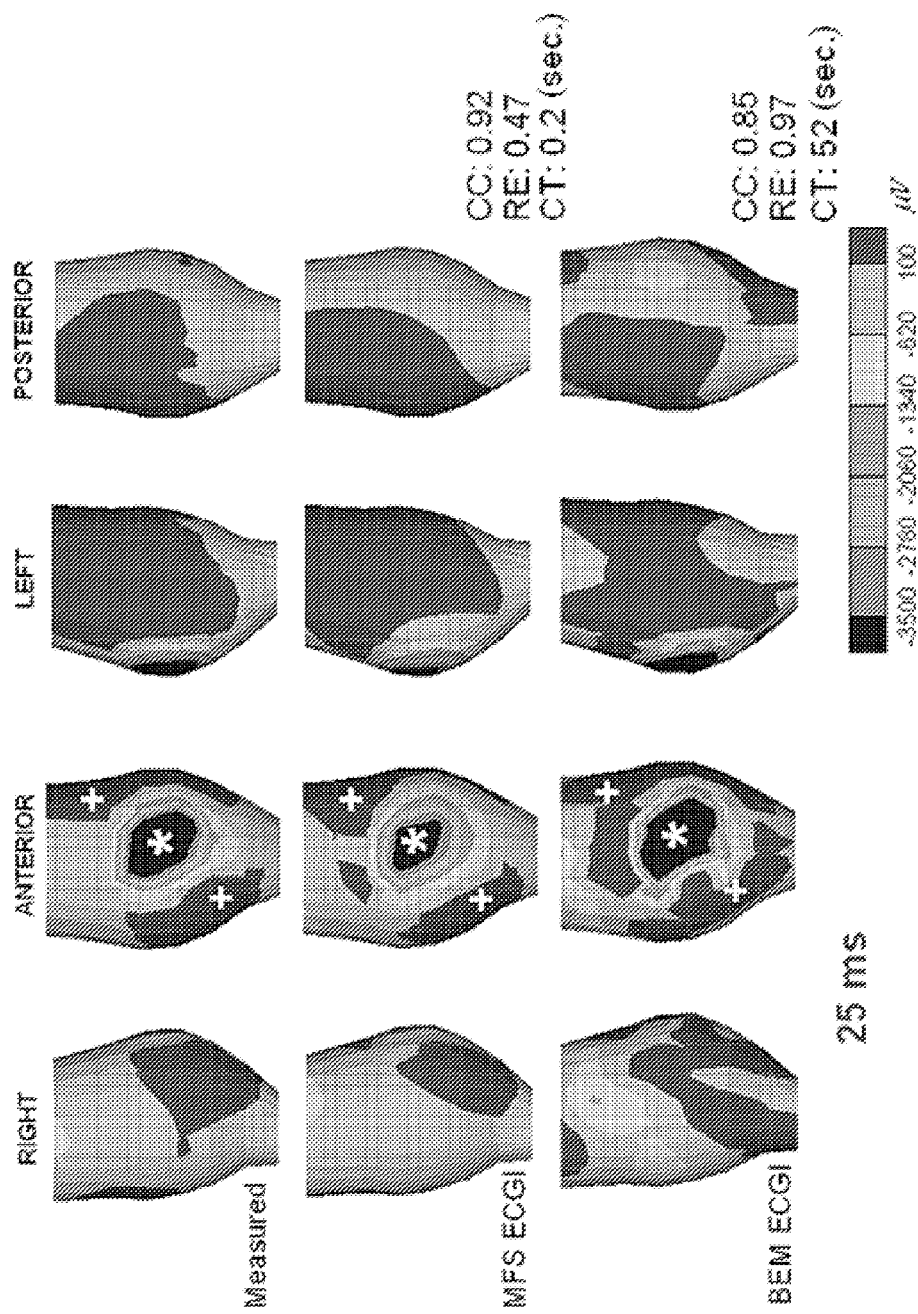
FIG. 9 depicts heart surface potential maps for directly-measured heart surface potentials, heart surface potentials reconstructed using MFS ECGI, and heart surface potentials reconstructed using BEM ECGI.

FIG. 9 shows electric potential maps 25 ms after pacing from a single site; the pacing site being marked by an asterisk. The top row of FIG. 9 shows directly (i.e., invasively) measured heart surface potentials. The middle row shows heart surface potentials that were reconstructed using the MFS ECGI technique of the present invention. The bottom row shows heart surface potentials that were reconstructed using the prior BEM ECGI technique. The pacing site reconstructed by MFS ECGI is located only about 4 mm from its measured location, at the center of the potential minimum (blue). As can be seen, the potentials reconstructed via MFS ECGI show a high level of correspondence with the directly measured potentials. The pacing site reconstructed by BEM ECGI is located about 6 mm from its measured location. Additional examples of the improved accuracy of MFS ECGI relative to BEM ECGI are shown in FIG. 9 via the higher correlation coefficient (CC) score and the lower relative error (RE) score. Moreover, not only do these results show that MFS ECGI is more accurate than BEM ECGI, but these results further confirm that MFS ECGI is considerably faster than BEM ECGI—the computation time per frame (CT) for MFS ECGI in this experiment is shown to be 0.2 seconds (versus 52 seconds for BEM ECGI). Appendix B describes how these CC and RE values were computed.

Figure 10:
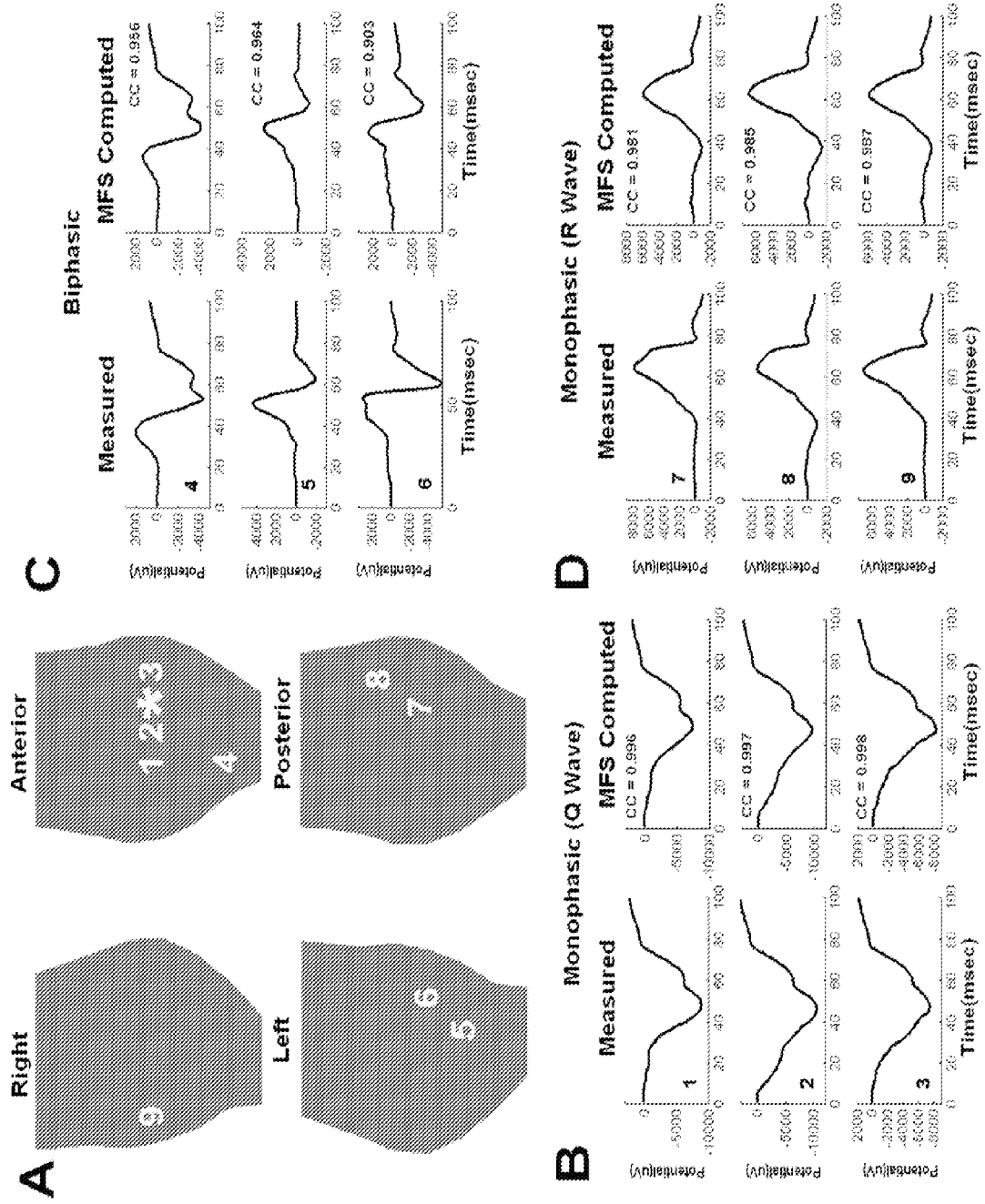
FIG. 10 depicts heart surface electrograms (both measured and reconstructed via MFS ECGI) from various locations on the heart surface for pacing from a single site.

As is known in the art, electrograms can be formed from heart surface potential maps by developing such maps over successive time frames and then organizing the time series of maps by epicardial location. FIGS. 10(A)-(D) show various electrograms derived in this manner. FIG. 10(A) shows four views of the epicardial cardiac surface. The numbers 1-9 in the boxes shown in FIG. 10(A) identify the locations of nine electrodes whose measured electrograms and MFS ECGI-reconstructed electrograms are displayed in FIGS. 10(B)-(D). Sites 1-3 are relatively close to the pacing site; sites 4-6 are relatively away from the pacing site; and sites 7-9 are relatively far away from the pacing site.

FIG. 10(B) depicts the monophasic negative (Q wave) electrograms from sites 1, 2 and 3 from both direct measurements and MFS ECGI reconstruction. FIG. 10(C) depicts the biphasic electrograms from sites 4, 5, and 6 from both direct measurements and MFS ECGI reconstruction. FIG. 10(D) depicts the monophasic positive (R wave) electrograms from sites 7, 8, and 9 from both direct measurements and MFS ECGI reconstruction. The displayed CC value in each MFS ECGI electrogram indicates the level of similarity between the MFS ECGI reconstructed electrograms and the directly measured electrograms. As can be seen, there is a high degree of correlation between the two.

Figure 11:
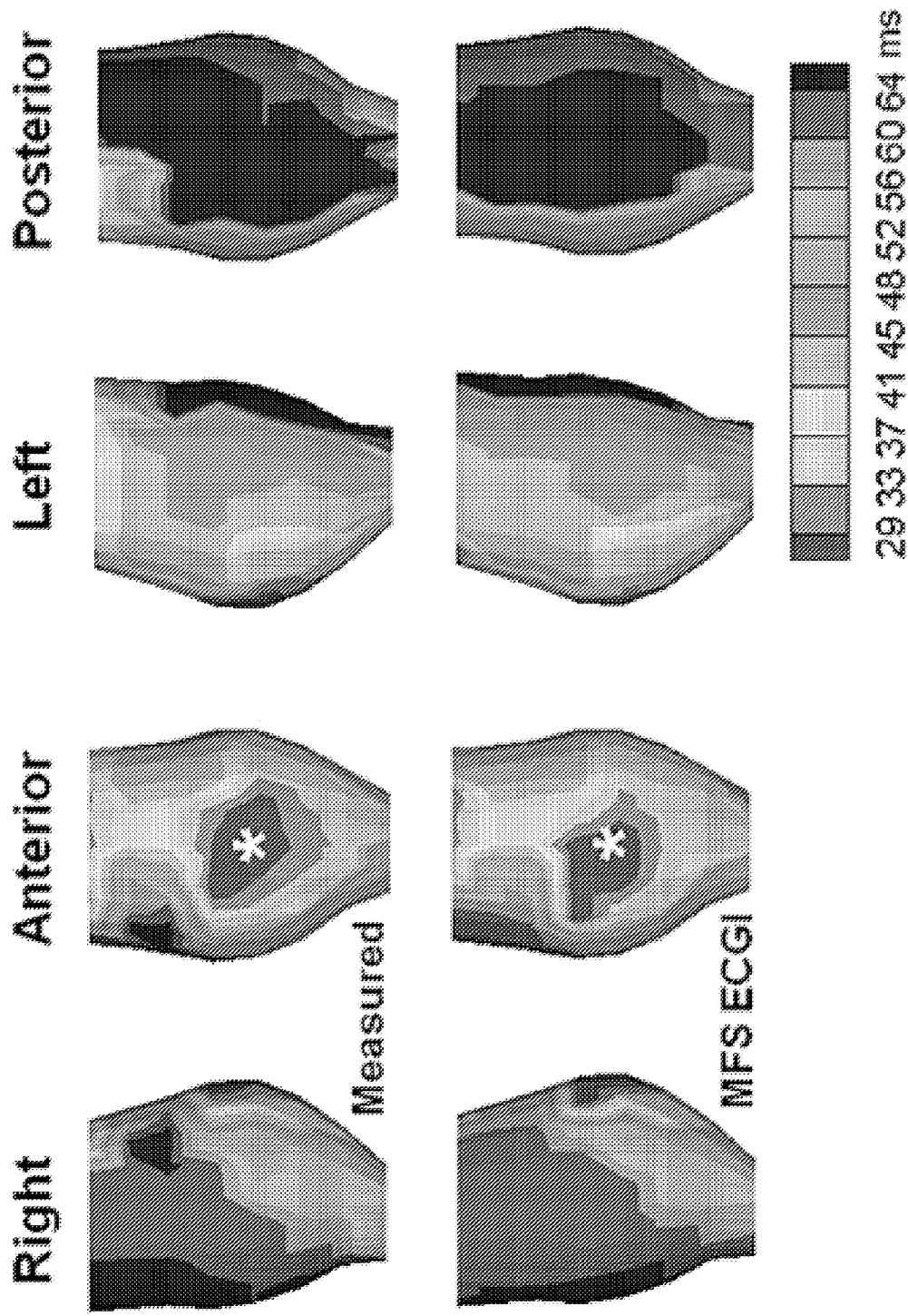
FIG. 11 depicts heart surface isochrone maps for pacing from a single site; both for measured potentials and for potentials reconstructed via MFS ECGI.

As is known in the art, isochrones for either measured or reconstructed epicardial cardiac surface potential data can be computed by taking the time of the epicardial activity at a given location as the time of maximum negative dV/dt of the temporal electrogram (which can be referred to as "intrinsic deflection") at that location. Isochrones provide a faithful and direct depiction of the epicardial activation sequence, which includes potential spatial non-uniformities of activation spread (e.g., regions of sparse or crowded isochrones depicting fast or slow speed respectively). FIG. 11 provides a comparison of heart surface isochrone maps developed from measured potentials (the top row of FIG. 11) and heart surface isochrone maps developed from potentials that have been reconstructed using MFS ECGI. As can be seen, the regions of earliest activation (shown in dark blue) are reproduced accurately in the MFS ECGI computed isochrone maps, as is the entire sequence of epicardial activation.

The development of optimal 3D surface meshes for the heart and torso geometry that is required by BEM ECGI is a difficult task. Non-optimal meshing will often introduce mesh-related artifacts in the BEM ECGI reconstructions, thereby decreasing the accuracy of BEM ECGI and hindering a physician's ability ECGI-reconstructed electrograms are displayed in FIGS. 10(B)-(D). Sites 1-3 are relatively close to the pacing site; sites 4-6 are relatively away from the pacing site; and sites 7-9 are relatively far away from the pacing site.

FIG. 10(B) depicts the monophasic negative (Q wave) electrograms from sites 1, 2 and 3 from both direct measurements and MFS ECGI reconstruction. FIG. 10(C) depicts the biphasic electrograms from sites 4, 5, and 6 from both direct measurements and MFS ECGI reconstruction. FIG. 10(D) depicts the monophasic positive (R wave) electrograms from sites 7, 8, and 9 from both direct measurements and MFS ECGI reconstruction. The displayed CC value in each MFS ECGI electrogram indicates the level of similarity between the MFS ECGI reconstructed electrograms and the directly measured electrograms. As can be seen, there is a high degree of correlation between the two.

As is known in the art, isochrones for either measured or reconstructed epicardial cardiac surface potential data can be computed by taking the time of the epicardial activity at a given location as the time of maximum negative dV/dt of the temporal electrogram (which can be referred to as "intrinsic deflection") at that location. Isochrones provide a faithful and direct depiction of the epicardial activation sequence, which includes potential spatial non-uniformities of activation spread (e.g., regions of sparse or crowded isochrones depicting fast or slow speed respectively). FIG. 11 provides a comparison of heart surface isochrone maps developed from measured potentials (the top row of FIG. 11) and heart surface isochrone maps developed from potentials that have been reconstructed using MFS ECGI. As can be seen, the regions of earliest activation (shown in dark blue) are reproduced accurately in the MFS ECGI computed isochrone maps, as is the entire sequence of epicardial activation.

Figure 12:
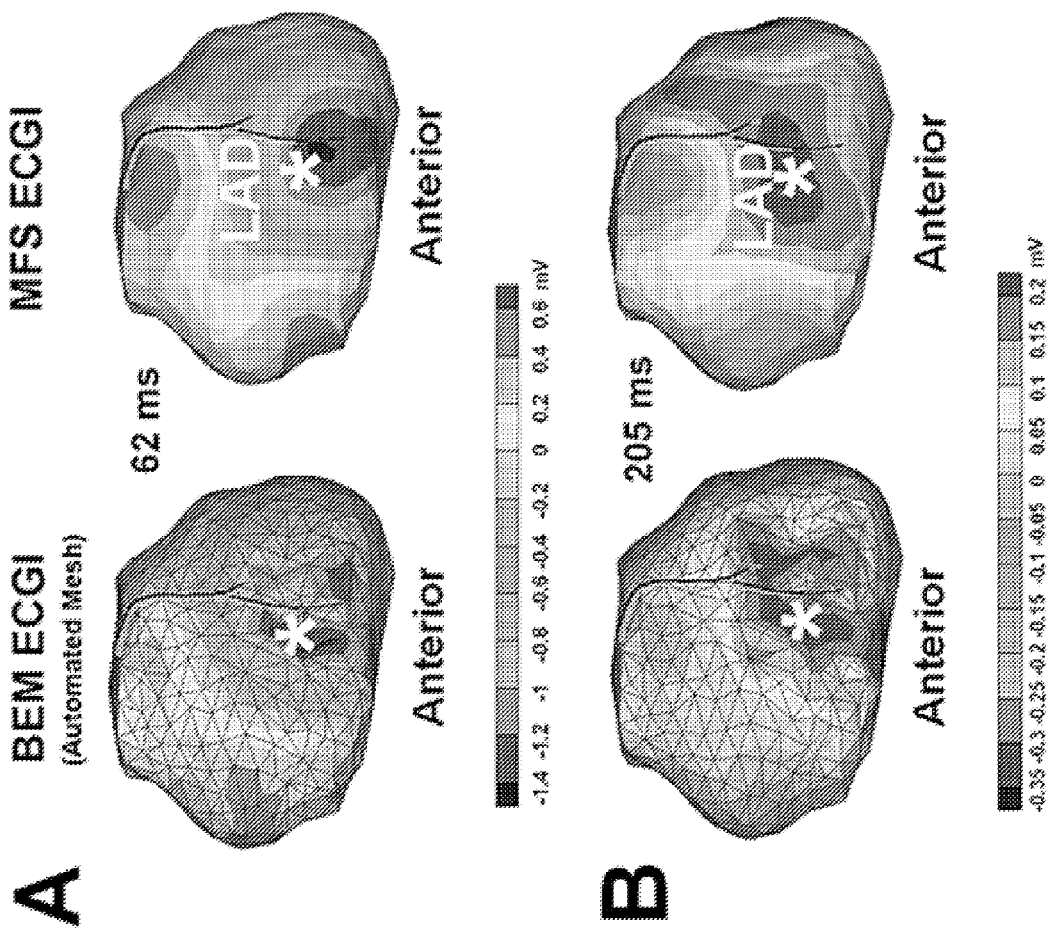
FIG. 12 depicts reconstruction results for a right ventricular epicardial pacing site in a human subject using both BEM ECGI and MFS ECGI, wherein the MFS ECGI reconstruction is shown to avoid mesh-related artifacts.

The development of optimal 3D surface meshes for the heart and torso geometry that is required by BEM ECGI is a difficult task. Non-optimal meshing will often introduce mesh-related artifacts in the BEM ECGI reconstructions, thereby decreasing the accuracy of BEM ECGI and hindering a physician's ability to interpret the reconstruction results. However, because MFS ECGI does not utilize a mesh to reconstruct epicardial cardiac surface potentials, it naturally avoids these mesh-related artifacts, which is a significant improvement over BEM ECGI. Panel A of FIG. 12 depicts heart surface potential maps 25 ms after right ventricular pacing from a single site (indicated by the white asterisk) in a human subject using both BEM ECGI and MFS ECGI, wherein the MFS ECGI reconstruction is shown to avoid mesh-related artifacts (the fragmentation of the minimum blue shown in the BEM ECGI panel). Panel B depicts these maps during repolarization. Avoidance of the mesh-related artifacts allows the pacing site to be more accurately located; wherein the error in locating the pacing site was 14 mm using BEM ECGI versus 7 mm using MFS ECGI.

Figure 13:
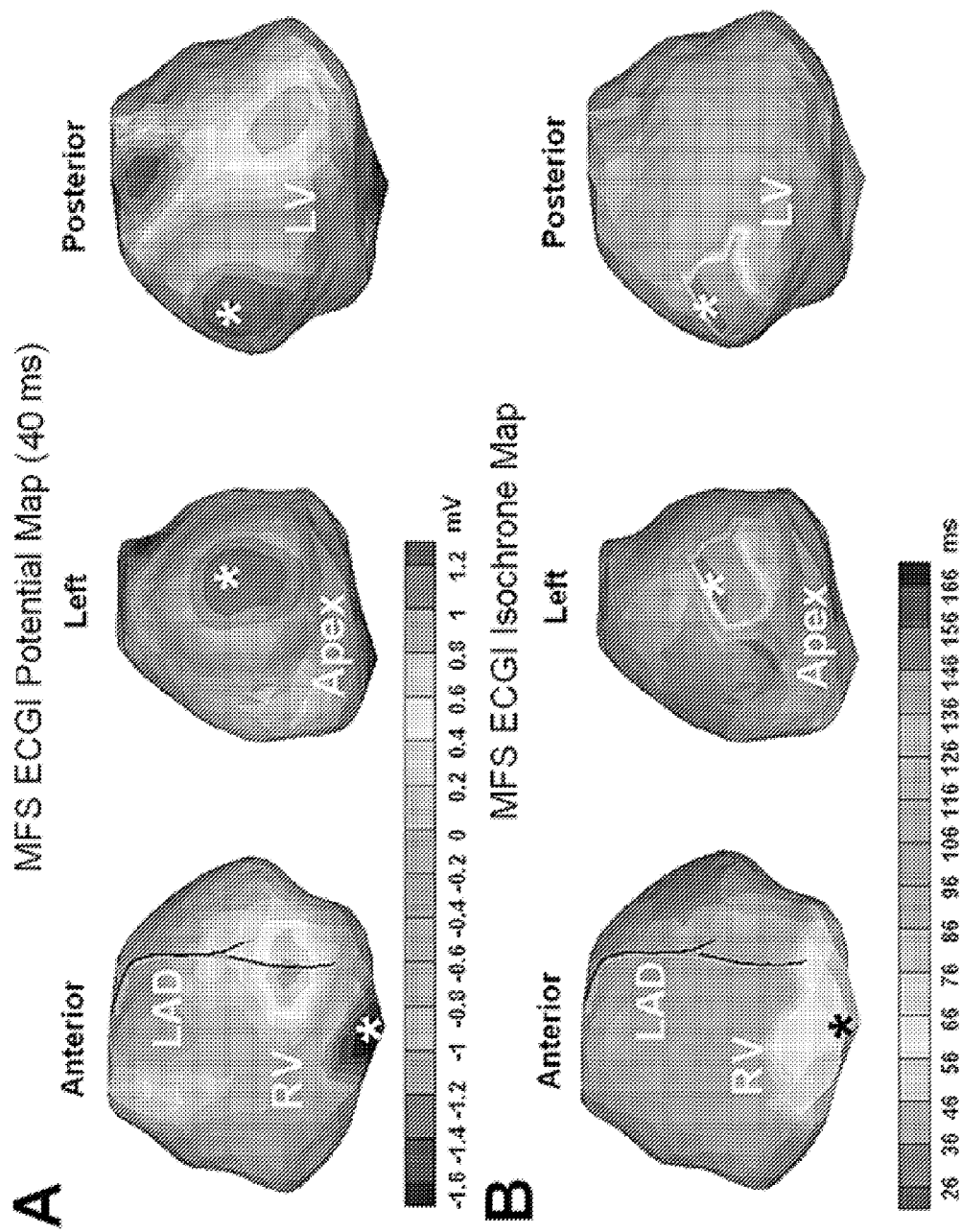
FIG. 13 depicts human heart surface isochrone maps and potential maps, using MFS ECGI, for pacing from both a right ventricle (RV) site and a left ventricle (LV) site.

Experimental Results—Human Biventricular Pacing:

Another area where MFS ECGI shows great promise is the investigation of heart activity patterns in cardiac resynchronization therapy (CRT) patients. CRT was recently introduced for chronic heart failure patients. However, the availability of information on both the electrical and mechanical behavior of the heart during CRT has been extremely limited because of previous inabilities to noninvasively map heart activity. However, with the development of MFS ECGI, an excellent tool is provided for investigating the heart activity patterns in CRT patients. FIG. 13 depicts human heart surface isochrone maps and potential maps, using MFS ECGI, for pacing from both a right ventricle (RV) site and a left ventricle (LV) (indicated by the asterisks). FIG. 13 demonstrates that in a CRT study, both LV and RV pacing sites can be accurately located using MFS ECGI. Experiments have shown that, with MFS ECGI, the location errors for the RV pacing site and the LV pacing site are 5.2 mm and 7.4 mm respectively.

Figure 14:
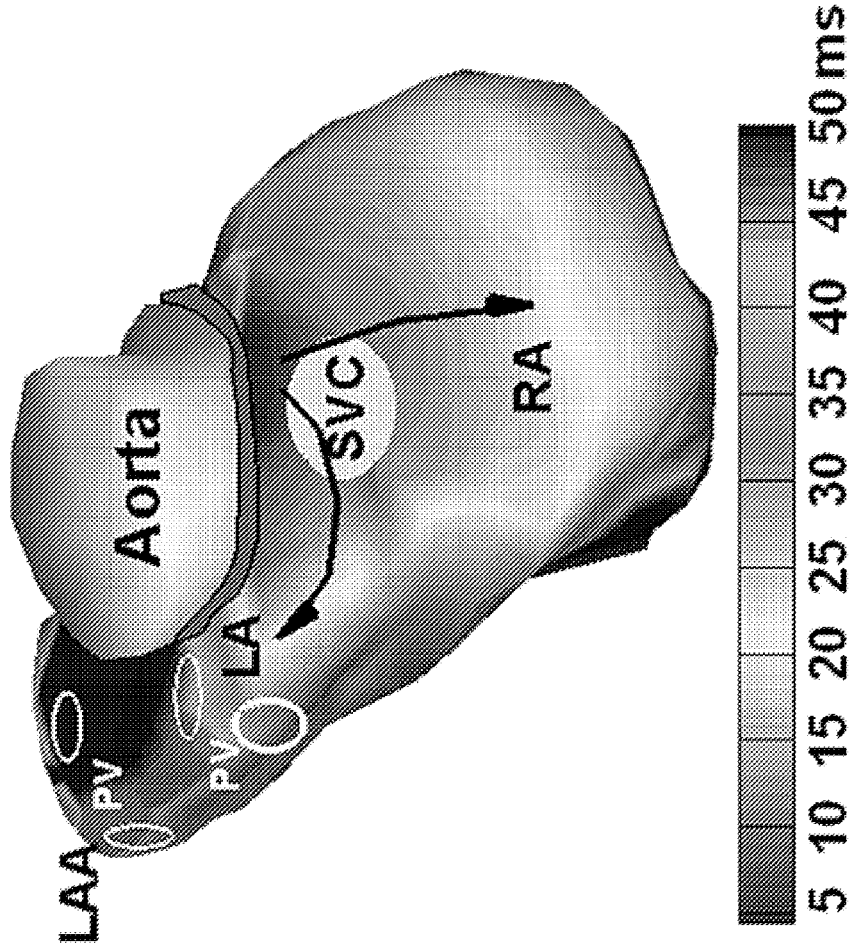
FIG. 14 depicts normal atrial activation isochrones, derived from potentials reconstructed via MFS ECGI.

Experimental Results—Human Normal Atria Activation:

As discussed above, the geometry of human atria are sufficiently complex that mesh-based methods such as BEM require significant time, human intervention, and computational resources to obtain an accurate 3D surface mesh. However, as mentioned above, MFS ECGI eliminates this meshing requirement and allows for faster and more accurate potential reconstructions. This is believed to be particularly true for complex atria geometry. FIG. 14 shows the normal atrial activation isochrones computed using MFS ECGI reconstructed potentials for a healthy volunteer. As can be seen, earliest activation starts in the right atrium (RA), near the anatomical location of the sinoatrial node (SA node). From the SA node, the impulse propagates to the left atrium (LA) and the rest of the RA. The LA appendage (LAA) is activated last. The abbreviation SVC in FIG. 14 refers to the superior vena cava and the abbreviation PV refers to the pulmonary veins. The inventors herein believe that the non-invasively reconstructed atrial isochrone produced by MFS ECGI is highly consistent with the invasive measurements as described in Durrer D. et al., *Total excitation of the isolated human heart*, Circulation, 1970, 41: 899-912, the entire disclosure of which is incorporated herein by reference.

While the present invention has been described above in relation to its preferred embodiment, various modifications may be made thereto that still fall within the invention's scope, as would be recognized by those of ordinary skill in the art. Such modifications to the invention will be recognizable upon review of the teachings herein.

For example, one could divide the volume between the torso surface and the heart surface into several compartments corresponding to the lungs, fat, bones, and so on, and apply MFS ECGI within each of these compartments. After doing so, the results for all of the compartments can be combined to obtain the reconstruction of epicardial cardiac surface potentials.

Furthermore, the inventors believe that the meshless technique described herein can be used to reconstruct electrical potentials for any volume field that can be described by the Laplace equation.

The inventors also believe that meshless techniques other than the MFS technique described herein can be used to practice meshless noninvasive ECGI in accordance with the present invention; these alternative meshless techniques include but are not limited to other implementations of MFS (such as MFS implementations using dipoles or multi-poles of higher order), the Radial Basis Function (RBF), the Boundary Knot (BKM) method, the Meshless Local Petrov-Galerkin (MLPG) method, the Trefftz method, the Element Free Galerkin (ELG) method, the Partition of Unity method (PUM, including PUFEM, GFEM and XFEM), and the Meshless Finite Element method (MFEM).

Further still, the inventors note that practitioners of the present invention may utilize different configurations of source nodes, different inverse matrix calculation methods (including all orders of Tikhonov regularization), different segmentation techniques, different geometry determining devices or make other changes as would be understood by a person having ordinary skill in the art following the teachings set forth herein. As such, the specific examples described in the specification correspond to preferred embodiments and are not meant to limit the invention beyond that which is claimed.

Additional information pertaining to ECGI, its principles of operation, and meshless algorithms can be found in the following publications, the entire disclosures of each of which are incorporated herein by reference:

Burnes et al., "A Noninvasive Imaging Modality for Cardiac Arrythmias", Circulation, pp. 2152-2158, Oct. 24, 2000;

Eisenberg, Anne, "Beyond the EKG, to a Hypersensitive Heart Monitor", The New York Times, Apr. 22, 2004;

Fairweather and Johnston, "The method of fundamental solutions for problems in potential theory", Treatment of Integral Equations by Numerical Methods, eds. Baker and Miller, Academic Press, London, pp. 349-359, 1982;

Fries and Matthies, "Classification and Overview of Mesh-free Methods", Institute of Scientific Computing, Technical University Braunschweig, Brunswick, Germany, Informatikbericht Nr.: 2003-3, July 2004 (revised);

Ghanem et al., "Heart-Surface Reconstruction and ECG Electrodes Localization Using Fluoroscopy, Epipolar Geometry and Stereovision: Application to Noninvasive Imaging of Cardiac Electrical Activity", IEEE Transactions on Medical Imaging, Vol. 22, No. 10, pp. 1307-1318, October 2003;

Golberg et al., "The method of fundamental solutions for diffusion equations", Boundary Element Technology XIII, eds. C. S. Chen, Wang and Rudy, "Application of the Method of Fundamental Solutions to Potential-based Inverse Electrocardiography", (expected to be published in the Annals of Biomedical Engineering in or around August 2006);

APPENDIX A

The method of fundamental solution (MFS) has been used in various mathematical and engineering applications to compute solutions of partial differential equations (PDE). See Y. C. Hon, T. Wei, A fundamental solution method for inverse heat conduction problem, *Engineering Analysis with Boundary Elements*, Vol. 28, Issue 5, pp. 489-495, 2004; Fairweather G, R. L. Johnston, The method of fundamental solutions for problems in fluid flow, *Appl. Math. Modeling*, 8, 265-270, 1984; and Golberg M A, Chen CS. The method of fundamental solutions for potential, Helmholtz and diffusion problems. In Boundary Integral Methods, Golberg M A ed.

*Computational Mechanics Publications*, 103-176, 1998, the entire disclosures of which are incorporated herein by reference.

MFS approximates the solution of a PDE by a linear combination of fundamental solutions of the governing partial differential operator. See, Fairweather G, Karageorghis A. The method of fundamental solutions for elliptic boundary value problems. *Adv Comput Math* 9(1-2): 69-95, 1998, the entire disclosure of which is incorporated herein by reference. For ECGI, the governing partial differential operator is the Laplacian operator $\nabla^2$. The formulation of MFS for a $\nabla^2$ boundary value problem is described below.

MFS has evolved from traditional boundary integral methods. The following example is used to describe the theoretical formulation of MFS for a Laplacian operator.

$$\nabla^2 u(x)=0, x \in \Omega \qquad (a1)$$

$$u(x)=b(x), x \in \Gamma, \Gamma=\partial\Omega \qquad (a2)$$

where $\nabla^2$ is the Laplace differential operator with a known fundamental solution f(r) in 3D space, and where b(x) is the Essential boundary condition. According to the definition of fundamental solution, the fundamental solution of the Laplace operator can be obtained by solving the following equations:

$$\nabla^2 f = \delta(r) \qquad (a3)$$

where $\delta(r)$ is the delta function, where $r=\|x-y\|$ is the 3D Euclid distance between point x and point y, and where x, y∈Ω;

According to Kythe P K, Fundamental Solutions for Differential Operators and Applications, Birkhauser: Boston, Basel, Berlin. 1996, the entire disclosure of which is incorporated herein by reference:

$$f(r) = \begin{cases} -\frac{1}{2\pi}\ln r, & 2D \\ \frac{1}{4\pi r}, & 3D \end{cases} \qquad (a4)$$

The traditional boundary integral approach is to represent solution u(x) in term of the double layer potential:

$$u(x) = \int_\Gamma \frac{\partial f(\|x-y\|)}{\partial n} e(y) dy, \quad x \in \Omega, \quad y \in \Gamma \qquad (a5)$$

where, n is the outward pointing normal at point y, and where e(y) is the unknown density function. See Patridge, P. W., Brebbia, C. A. & Wrobel, L. C., The Dual Reciprocity Boundary Element Method, *Computational Mechanics Publications*, Southampton and Elsevier, London, 1992; and Golberg, M. A., Chen, C. S., Discrete Projection Methods for Integral Equations, *Computational Mechanics Publications*, Southampton, 1996, the entire disclosures of which are incorporated herein by reference. In recent years, the single layer potential representation of u(x) for (a1)-(a2) has appeared in a substantial amount of work:

$$u(x)=\int_\Gamma f(\|x-y\|)e(y)dy, x \in \Omega, y \in \Gamma \qquad (a6)$$

See Golberg, M. A., Chen, C. S., Discrete Projection Methods for Integral Equations, *Computational Mechanics Publications*, Southampton, 1996; Chen, Y., Atkinson, K. E., Solving a Single Layer Integral Equation on Surface in R3, the University of Iowa, Department of Mathematics, Technical Report, No 51, 1994, the entire disclosures of which are incorporated herein by reference.

The source density distribution e(y) can be determined by solving the following equation under the assumption of a double layer:

$$\int_\Gamma \frac{\partial f(\|x-y\|)}{\partial n} e(y) dy = b(x), \quad x \in \Gamma, \quad y \in \Gamma \qquad (a7)$$

or under the assumption of a single layer:

$$\int_\Gamma f(\|x-y\|)e(y)dy=b(x), x \in \Gamma, y \in \Gamma \qquad (a8)$$

However the singular integrals are involved in both cases, which become the most difficult part in solving the problem. To alleviate the difficulties of singular integrals, the following formulation (similar to the single layer potential in (a6)) was considered in Karageorghis, A., Fairweather, G., The method of fundamental solutions for the numerical solution of the biharmonic equation, Journal of Computational Physics, 69, 435-459, 1987, the entire disclosure of which is incorporated herein by reference, i.e., $$u(x)=\int f(\|x-y\|)e(y)dy, x \in \Omega, y \in \hat{\Gamma} \qquad (a9)$$

where boundary $\hat{\Gamma}$ is the surface of the domain $\hat{\Omega}$ containing Ω as shown below.

Because $f(\|x-y\|)$ is the fundamental solution of the Laplace operator as shown in equation (a3), (a9) satisfies the differential Equation (a1) automatically. Therefore we need only to force the boundary condition (a2), which means:

$$\int f(\|x-y\|)e(y)dy=b(x), x \in \Gamma, y \in \hat{\Gamma} \qquad (a10)$$

where source density distribution e(y), y∈$\hat{\Gamma}$, is to be determined. Once the source density is determined, the solution of (a1)-(a2) is solved. The analytic integral representation of (a10) means that there are infinite number of source density points on $\hat{\Gamma}$. Therefore, in order to apply numerical solution method, it is necessary to discretize e(y).

Assume $\psi_j(y)$, j=1, 2, . . . ∞ is a complete set of functions on $\hat{\Gamma}$, e(y) can be approximated by:

$$e(y) = \sum_{j=1}^n c_j \psi_j(y), \quad y \in \hat{\Gamma} \qquad (a11)$$

Substituting (a11) into (a10) and collocating at n points on $x_k \in \Gamma$, k=1, 2, . . . n; we have $$\sum_{j=1}^n c_j \int_{\hat{\Gamma}} f(\|x_k - y\|)\psi_j(y) dy = b(x_k), 1 \le k \le n, y \in \hat{\Gamma} \qquad (a12)$$

Since the fictitious boundary $\hat{\Gamma}$ located outside the physical domain, the integrand $f(\|x_k-y\|)$ is nonsingular and standard quadrature rules can be used giving $$\int_{\hat{\Gamma}} f(\|x_k - y\|)\psi_j(y) dy \approx \sum_{i=1}^M w_i f(\|x_k - y_i\|)\psi_j(y), \qquad (a13)$$

$$y_i \in \hat{\Gamma}, i = 1, 2, \dots, M$$

From (a12) and (a13), we can obtain:

$$\sum_{j=1}^{n} c_j \sum_{i=1}^{M} w_i f(\|x_k - y_i\|) \psi_j(y_i) = \sum_{i=1}^{M} w_i \left[ \sum_{j=1}^{n} c_j \psi_j(y_i) \right] f(\|x_k - y_i\|) = b(x_k), \quad 1 \le k \le n. \tag{a14}$$

Then:

$$\sum_{i=1}^{M} a_i f(\|x_k - y_i\|) = b(x_k), \quad 1 \le k \le n. \tag{a15}$$

where:

$$a_i = w_i \sum_{j=1}^{n} c_j \psi_j(y_i) \tag{a16}$$

We can find (a15) is equivalent to approximate the solution to (a1) by $$u_a(x) = \sum_{j=1}^{M} a_j f(\|x - y_j\|), x \in \Gamma, y_j \in \hat{\Gamma} \tag{a17}$$

For completeness, a constant coefficient is added into (17):

$$u_a(x) = a_0 + \sum_{j=1}^{M} a_j f(\|x - y_j\|), x \in \Gamma, y_j \in \hat{\Gamma} \tag{a18}$$

The above mathematical formulation (a18) is referred to as Method of Fundamental Solution (MFS). See Golberg M A, Chen CS. The method of fundamental solutions for potential, Helmholtz and diffusion problems. In Boundary Integral Methods, Golberg M A ed. *Computational Mechanics Publications,* 103-176, 1998, the entire disclosure of which is incorporated herein by reference. As we can see in (a18), the approximate solution $u_a$ can be represented by a linear combination of fundamental solutions of the governing equation with the singularities $y_j$, $j=1, 2, \ldots$ M. placed outside the domain of the problem.

It is important to note that the MFS is applicable to different types of boundary conditions. For Natural boundary condition, if the point x lies on the boundary of solution domain, then the gradient along the outward normal to the boundary at x is given by:

$$\frac{\partial}{\partial n} u_a(x) = \sum_{j=1}^{M} a_j \frac{\partial}{\partial n} f(\|x - y_j\|), x \in \Gamma, y_j \in \hat{\Gamma}. \tag{a19}$$

where source density distribution e(y), $y \in \hat{\Gamma}$, is to be determined. Once the source density is determined, the solution of (a1)-(a2) is solved. The analytic integral representation of (a10) means that there are infinite number of source density points on $\hat{\Gamma}$. Therefore, in order to apply numerical solution method, it is necessary to discretize e(y).

Assume $\psi_j(y)$, $j=1, 2, \ldots \infty$ is a complete set of functions on $\hat{\Gamma}$, e(y) can be approximated by:

$$e(y) = \sum_{j=1}^{n} c_j \psi_j(y), y \in \hat{\Gamma} \tag{a11}$$

Substituting (a11) into (a10) and collocating at n points on $x_k \in \vartheta$, $k=1, 2, \ldots n$; we have $$\sum_{j=1}^{n} c_j \int_{\hat{\Gamma}} f(\|x_k - y\|) \psi_j(y) dy = b(x_k), \quad 1 \le k \le n, y \in \hat{\Gamma} \tag{a12}$$

Since the fictitious boundary $\hat{\Gamma}$ located outside the physical domain, the integrand $f(\|x_k - y\|)$ is nonsingular and standard quadrature rules can be used giving $$\int_{\hat{\Gamma}} f(\|x_k - y\|) \psi_j(y) dy \approx \sum_{i=1}^{M} w_i f(\|x_k - y_i\|) \psi_j(y), \tag{a13}$$

$$y_i \in \hat{\Gamma}, i = 1, 2, \ldots, M$$

From (a12) and (a13), we can obtain:

$$\sum_{j=1}^{n} c_j \sum_{i=1}^{M} w_i f(\|x_k - y_i\|) \psi_j(y_i) = \sum_{i=1}^{M} w_i \left[ \sum_{j=1}^{n} c_j \psi_j(y_i) \right] f(\|x_k - y_i\|) = b(x_k), \quad 1 \le k \le n. \tag{a14}$$

Then:

$$\sum_{i=1}^{M} a_i f(\|x_k - y_i\|) = b(x_k), 1 \le k \le n. \tag{a15}$$

Therefore the Natural boundary condition:

$$\frac{\partial}{\partial n} u(x) = i(x), \quad x \in \Gamma, \Gamma = \partial \Omega \tag{a20}$$

can be discretized and expressed as:

$$\sum_{i=1}^{M} a_i \frac{\partial}{\partial n} f(\|x_k - y_j\|) = i(x_k), x_k \in \Gamma, \tag{a21}$$

$$k = 1, 2, \ldots, n, y_j \in \hat{\Gamma}, j = 1, 2, \ldots, M;$$

APPENDIX B

For the tank-torso protocols, statistical measurements in terms of relative error (RE) and correlation coefficients (CC) were computed with respect to the measured data to quantitatively evaluate the accuracy of ECGI. RE gives an estimate of the amplitude difference and CC gives an estimate of the similarity of potential patterns or electrogram morphologies between the measured and computed data:

$$RE = \sqrt{\frac{\sum_{i=1}^{n}(V_i^C - V_i^M)^2}{\sum_{i=1}^{n}(V_i^M)^2}}$$

$$CC = \frac{\sum_{i=1}^{n}(V_i^M - \overline{V}^M)(V_i^C - \overline{V}^C)}{\sqrt{\sum_{i=1}^{n}(V_i^M - \overline{V}^M)^2}\sqrt{\sum_{i=1}^{n}(V_i^C - \overline{V}^C)^2}}$$

where n is the number of nodes (points at which epicardial potentials are computed). For electrograms, n is the number of time frames. $V_i^C$ is the computed potential for node i, $V_i^M$ is the measured potential for node i, $\overline{V}^M$ is the average measured potential, and $\overline{V}^C$ is the average computed potential.

In addition to CC and RE, pacing site localization errors (distance between computed and measured locations) are also provided for both torso-tank and human reconstructions. The computed pacing site location was estimated by the center of an ellipse that best fits the quasi-elliptical negative potential region that develops around the pacing site. The earliest time frame after pacing, for which such pattern was present, was used for this purpose. Pacing sites could also be determined from isochrone maps as the sites of earliest activation.

Qualitative evaluations of ECGI reconstructions are conducted by visual comparison to measured data (torso-tank experiments) and to well established potentials, electrograms and isochrone patterns associated with pacing (human subjects).

In addition to CC RE, clinical application of ECGI will benefit from computational efficiency that reconstructs epicardial potentials in close to real time (near real time). Although regularization procedures (e.g. Tikhonov regularization with the regularization parameter selected by CRESO, and so on) can be done close to real-time, forming the coefficient matrix usually still takes more than 1 minute in BEM ECGI. Ideally if the coefficient matrix can also be formed within less time (e.g. less than one second), ECGI would have much better chance to be used in the interactive applications during clinical interventions. In order to evaluate the speed of forming the coefficient matrix for BEM ECGI and MFS ECGI, Computation Time (CT) and Computation Time Ratio (CTR) between MFS ECGI and BEM ECGI are defined as:

CT=Computation time of forming coefficient matrix (in seconds)

$$CTR = \frac{CT \text{ of } BEM \text{ } ECGI}{CT \text{ of } MFS \text{ } ECGI}$$

CT and CRT were computed on a laptop with Pentium Mobile 1.7 GHz and 1G RAM. Qualitative evaluations of automatic between MFS ECGI and BEM ECGI were also done by comparing the working procedure of MFS ECGI and BEM ECGI in specific cases.

The invention claimed is:

1. A noninvasive system for determining electrical activity for a heart of a living being, the system comprising:
memory to store computer-readable instructions; and
a processor configured to access the memory and execute the computer readable instructions to compute heart electrical activity data that represents heart electrical activity of the living being from a set of noninvasively measured body surface electrical potentials using data that describes a geometric relationship between a plurality of locations corresponding to where the body surface electrical potentials were measured and a surface representation of the heart;
wherein the processor executes the computer readable instructions to compute the heart electrical activity data by translating the measured body surface electrical potentials to surface potentials on the surface representation of the heart without using a mesh of any heart surface.

2. The system of claim 1 wherein the heart electrical activity data comprises a set of epicardial envelope electrical potentials.

3. The system of claim 2 wherein the processor is further configured to meshlessly compute the set of epicardial envelope electrical potentials via a method of fundamental solution (MFS).

4. The system of claim 2 wherein the living being comprises a torso having a body surface, the system further comprising:
an electrode array system in communication with the processor for noninvasively measuring electrical potentials at a plurality of locations on the torso body surface via a plurality of electrodes applied to the torso to provide a set of noninvasively measured body surface potentials;
a geometry determining device in communication with the processor, the geometry determining device being configured to (1) determine a geometry of the locations on the body surface where the electrical potentials were noninvasively measured, (2) determine a geometry of a heart surface of the living being, and (3) communicate the determined geometries of the locations on the body surface and the heart surface to the processor; and
wherein the processor is further configured to compute the set of epicardial envelope electrical potentials from the set of noninvasively measured body surface potentials and the determined geometries.

5. The system of claim 4 wherein the processor is further configured to compute the set of the epicardial cardiac surface electrical potentials in near-real time.

6. The system of claim 4 wherein the processor is further configured to (1) determine a plurality of epicardial nodes that define locations on an epicardial cardiac surface for which the computed epicardial cardiac surface electrical potentials apply, (2) determine a plurality of source nodes, wherein a plurality of the source nodes define a plurality of locations along a surface outside the torso and wherein another plurality of the source nodes define a plurality of locations along a surface inside the epicardial cardiac surface, (3) determine a matrix of coefficients A that relates each electrode location to each source node location, (4) perform an inverse computation on the matrix of coefficients A and the noninvasively measured body surface potentials to compute a plurality of source node coefficients, (5) determine a matrix of coefficients B that relates each epicardial node location to each source node location, and (6) perform a forward computation using the matrix of coefficients B and the source node coefficients to compute the set of epicardial cardiac surface electrical potentials.

7. The system of claim 6 wherein the processor is further configured to dynamically determine the source nodes.

8. The system of claim 6 wherein the processor is further configured to statically determine the source nodes by (1) defining each source node that is outside the body surface such that it is located a predetermined distance outward from a corresponding electrode location on a ray extending from a calculated center of the epicardial cardiac surface through a corresponding electrode location, and (2) defining each source node that is inside the epicardial cardiac surface such that it is located a predetermined distance inward from a corresponding epicardial node location on a ray extending from the calculated center of the epicardial cardiac surface through the corresponding epicardial node location.

9. The system of claim 6 wherein the processor is further configured to generate an epicardial cardiac surface potential map from the set of computed epicardial cardiac surface electrical potentials.

10. The system of claim 6 wherein the processor is further configured to compute a plurality of sets of the epicardial cardiac surface electrical potentials over a time duration from a plurality of successively noninvasively measured body surface electrical potentials.

11. The system of claim 10 wherein the processor is further configured to generate at least one selected from the group consisting of a plurality of electrograms and an isochrone from the sets of computed epicardial cardiac surface electrical potentials.

12. The system of claim 10 wherein the processor is further configured to generate, from the sets of computed epicardial cardiac surface electrical potentials, at least one selected from the group consisting of a recovery map, an integral map, and an activation-recovery interval map.

13. The system of claim 1 wherein the processor is integrated into a medical imaging platform.

14. A method for noninvasively reconstructing electrical activity of a heart of a living being, the living being having a body surface, the method comprising:
    computing heart electrical activity data corresponding to heart electrical activity from a set of noninvasively measured body surface electrical potentials via an algorithm that translates the noninvasively measured body surface electrical potentials to the heart electrical activity data, the algorithm not using a mesh of any heart surface and not using a mesh of the body surface; and
    generating a display based on the heart electrical activity data.

15. The method of claim 14 wherein the algorithm comprises a method of fundamental solution (MFS).

16. The method of claim 14 further comprising:
    noninvasively measuring electrical potentials at a plurality of locations on the body surface;
    determining a geometry of the plurality of locations on the body surface where the electrical potentials were noninvasively measured; and
    determining a geometry of an epicardial envelope of the living being; and
    wherein the computing comprises computing epicardial envelope electrical potential estimates from the set of noninvasively measured body surface potentials and the determined geometries of the plurality of locations on the body surface and the epicardial envelope.

17. The method of claim 16 wherein the computing further comprises:
    configuring a plurality of epicardial nodes that define the locations on the epicardial envelope for which the computed epicardial envelope electrical potential estimates apply;
    configuring a plurality of source nodes, wherein a plurality of the source nodes define a plurality of locations along a surface outside a torso of the living being and wherein another plurality of the source nodes define a plurality of locations along a surface inside the epicardial envelope;
    determining a matrix of coefficients A that relates each electrode location to each source node location;
    performing an inverse computation on the matrix of coefficients A and the noninvasively measured body surface electrical potentials to compute a plurality of source node coefficients;
    determining a matrix of coefficients B that relates each epicardial node location to each source node location; and
    performing a forward computation using the matrix of coefficients B and the source node coefficients to compute the epicardial envelope electrical potential estimates.

18. The method of claim 17 wherein the source node configuring comprises (1) defining each source node that is outside the torso such that it is located a predetermined distance outward from a corresponding electrode location on a ray extending from a calculated center of the epicardial envelope through the corresponding electrode location, and (2) defining each source node that is inside the heart surface such that it is located a predetermined distance inward from a corresponding epicardial node location on a ray extending from the calculated center of the epicardial envelope through the corresponding epicardial node location.

19. The method of claim 17 further comprising:
    generating an epicardial cardiac surface potential map from the computed epicardial cardiac surface electrical potential estimates.

20. A non-transitory computer readable medium for use in connection with noninvasively computing electrical activity of a heart of a living being, the living being having a body surface, the computer readable medium comprising:
    a code segment executable by a processor for computing data corresponding to heart electrical activity from a set of noninvasively measured body surface electrical potentials via a meshless algorithm that translates the noninvasively measured body surface electrical potentials to the heart electrical activity data;
    a code segment executable by a processor for determining a geometry of locations on the body surface where the body surface electrical potentials were noninvasively measured; and
    a code segment executable by a processor for determining a geometry of an epicardial envelope of the living being; and
    wherein the computing code segment is configured to compute the set of epicardial envelope electrical potentials from the set of noninvasively measured body surface potentials and the determined geometries.

21. The computer readable medium of claim 20 wherein the meshless algorithm comprises a method of fundamental solution (MFS).

22. The computer readable medium of claim 20 wherein the body surface comprises the torso of the living being, and wherein the locations on the body surface where the set of noninvasively measured body surface electrical potentials were noninvasively measured correspond to locations of a plurality of electrodes that are applied to the living being's torso.

23. The computer readable medium of claim 20 wherein the computing code segment further comprises:

a code segment executable by a processor for defining a plurality of epicardial nodes that correspond to the locations on the epicardial envelope for which the computed epicardial envelope electrical potentials apply;

a code segment executable by a processor for defining a plurality of source nodes, wherein a plurality of the source nodes correspond to a plurality of locations along a surface outside the torso and wherein another plurality of the source nodes correspond to a plurality of locations along a surface inside the epicardial envelope;

a code segment executable by a processor for determining a matrix of coefficients A that relates each electrode location to each source node location;

a code segment executable by a processor for performing an inverse computation on the matrix of coefficients A and the noninvasively measured body surface electrical potentials to compute a plurality of source node coefficients;

a code segment executable by a processor for determining a matrix of coefficients B that relates each epicardial node location to each source node location; and a code segment executable by a processor for performing a forward computation using the matrix of coefficients B and the source node coefficients to compute the set of epicardial envelope electrical potentials.

24. The computer readable medium of claim 23 wherein the heart has an epicardial cardiac surface, wherein the epicardial envelope electrical potentials comprise a set of epicardial cardiac surface electrical potentials, and wherein the code segment for defining epicardial nodes is further configured to define the epicardial nodes such that they correspond to the locations on the epicardial cardiac surface for which the computed epicardial cardiac surface electrical potentials apply.

25. The computer readable medium of claim 24 wherein the source node configuring code segment is configured to statically define the source nodes.

26. The computer readable medium of claim 25 wherein the statically defining code segment is configured to (1) define each source node that is outside the torso surface such that it is located a predetermined distance outward from a corresponding electrode location on a ray extending from a calculated center of the epicardial cardiac surface through the corresponding electrode location, and (2) define each source node that is inside the epicardial cardiac surface such that it is located a predetermined distance inward from a corresponding epicardial node location on a ray extending from the calculated center of the epicardial cardiac surface through the corresponding epicardial node location.

27. A method for reconstructing electrical potentials on a surface inside a volume, wherein the volume comprises a field that satisfies Laplace equation, the volume having an outer surface, the method comprising:

computing data corresponding to a plurality of electrical potentials on a surface inside the volume from a set electrical potentials measured at the volume's outer surface via a meshless algorithm that translates the measured outer surface electrical potentials to the inside surface electrical potential data without using a mesh of the surface inside the volume and without using a mesh of the outer surface of the volume; and generating a display based on the heart electrical activity data.

28. The method of claim 27 wherein the inside surface electrical potential data comprises a plurality of electrical potentials at different locations along the inside surface.

29. The method of claim 28 further comprising:
applying a plurality of electrodes to the outer surface to measure the outer surface electrical potentials;

defining a plurality of inside surface nodes that correspond to the locations on the inside surface for which the computed inside surface electrical potentials apply;

defining a plurality of source nodes, wherein a plurality of the source nodes correspond to a plurality of locations along a surface outside the outer surface and wherein another plurality of the source nodes correspond to a plurality of locations along a surface inside the inside surface;

determining a matrix of coefficients A that relates each outer surface location where an outer surface electrical potential was measured to each source node location;

performing an inverse computation on the matrix of coefficients A and the measured outer surface electrical potentials to compute a plurality of source node coefficients;

determining a matrix of coefficients B that relates each inside surface node location to each source node location; and performing a forward computation using the matrix of coefficients B and the source node coefficients to compute the inside surface electrical potentials.

30. The method of claim 27 wherein the volume comprises a human torso.

31. The method of claim 27 wherein the inside surface comprises a human epicardial cardiac surface, and wherein the meshless algorithm comprises a method of fundamental solution (MFS).

32. A system for reconstructing heart electrical activity for a heart of a living being, the living being having a torso, the torso having an outer surface, the system comprising:

memory to store computer-readable instructions; and a processor configured to access the memory and execute the computer readable instructions to (1) receive data representing a plurality of electrical potentials measured on the torso outer surface at a plurality locations along the torso outer surface, (2) receive spatial relationship data that describes a spatial relationship between the torso outer surface and an epicardial envelope, (3) determine the torso outer surface locations where the electrical potentials were measured, (4) define a plurality of locations along the epicardial envelope, (5) define a plurality of source node locations outside the torso outer surface, (6) define a plurality of source node locations inside the epicardial envelope, (7) based at least in part upon the spatial relationship data, the determined torso outer surface locations, and the defined source node locations, compute a matrix of coefficients A that spatially relates each determined torso outer surface location to each defined source node location, (8) perform an inverse computation on A and the received electrical potential data to compute a plurality of source node location coefficients, (9) based at least in part upon the spatial relationship data, the defined epicardial envelope locations, and the defined source node locations, compute a matrix of coefficients B that relates each defined epicardial envelope location to each defined source node location, (10) perform a forward computation using B and the source node coefficients to compute electrical activity data that represents electrical activity on the epicardial envelope, and (11) store the electrical activity data in the memory.

33. The system of claim 32 further comprising:
- a plurality of electrodes for application to the torso outer surface to measure electrical potentials at the plurality of torso outer surface locations; and
- a signal acquisition and processing device, wherein the electrodes are in communication with the processor via the signal acquisition and processing device, the signal acquisition and processing device being configured to acquire and process the measured electrical potentials to a data format suitable for processing by the processor.

34. The system of claim 33 further comprising a geometry determining device in communication with the processor, the geometry determining device being configured to acquire and provide the spatial relationship data to the processor.

35. The system of claim 33 wherein the processor is further configured to automatically define the plurality of epicardial envelope locations.

36. The system of claim 35 wherein the processor is further configured to automatically define the plurality of epicardial envelope locations by evenly distributing the defined epicardial envelope locations along the epicardial envelope.

37. A non-transitory computer readable medium having computer executable instructions for performing a method that comprises:

computing heart electrical activity data that represents heart electrical activity from a set of noninvasively measured body surface electrical potentials using data that describes a geometric relationship between a plurality of locations corresponding to where the body surface electrical potentials were measured and a representation of a surface of a heart of a living being, wherein the computing comprising:
- performing a first computation on a first transfer matrix and the noninvasively measured body surface electrical potentials to compute a first plurality of coefficients, the first computation being performed without using a mesh of any heart surface; and
- performing a second computation using a second transfer matrix and the first plurality of coefficients to compute a set of cardiac surface electrical potentials for the representation of the surface of the heart, the second computation being performed without using a mesh of any heart surface,
- the set of cardiac surface electrical potentials for the representation of the surface of the heart being stored in memory.

* * * * *